United States Patent
Hubbard et al.

(10) Patent No.: US 12,283,148 B2
(45) Date of Patent: *Apr. 22, 2025

(54) FUNCTIONAL CONTROL AND AGE VERIFICATION OF ELECTRONIC DEVICES THROUGH VISUAL COMMUNICATION

(71) Applicant: RAI Strategic Holdings, Inc., Winston-Salem, NC (US)

(72) Inventors: Sawyer Hubbard, Winston-Salem, NC (US); Charles A. Leyes, Winston-Salem, NC (US); Vince Ireland, Winston-Salem, NC (US); Sean Daugherty, Winston-Salem, NC (US); Sean Lukan, Winston-Salem, NC (US); Jared Aller, Winston-Salem, NC (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/381,464

(22) Filed: Oct. 18, 2023

(65) Prior Publication Data

US 2024/0046728 A1 Feb. 8, 2024

Related U.S. Application Data

(63) Continuation of application No. 17/548,415, filed on Dec. 10, 2021, now Pat. No. 12,087,117, which is a
(Continued)

(51) Int. Cl.
*G07C 9/32* (2020.01)
*H02J 7/00* (2006.01)
*H04L 9/40* (2022.01)

(52) U.S. Cl.
CPC .............. *G07C 9/32* (2020.01); *H02J 7/0042* (2013.01); *H04L 63/08* (2013.01); *H02J 7/00045* (2020.01)

(58) Field of Classification Search
CPC ........................................................ G07C 9/32
See application file for complete search history.

(56) References Cited

U.S. PATENT DOCUMENTS

| 8,244,216 B1 | 8/2012 | Becker |
| 10,531,693 B1 | 1/2020 | Greenbaum |
(Continued)

FOREIGN PATENT DOCUMENTS

| CN | 203446536 U | 2/2014 |
| CN | 104321779 A | 1/2015 |
(Continued)

OTHER PUBLICATIONS

International Search Report and Written Opinion from related international application PCT/US2020/026176, mailed on Sep. 11, 2020, all pages cited in its entirety.
(Continued)

*Primary Examiner* — Nabil H Syed
(74) *Attorney, Agent, or Firm* — Burr & Forman LLP

(57) ABSTRACT

An aerosol delivery or electronic nicotine delivery systems ("ENDS") device may include smoking articles that produce aerosol. The device may operate upon authentication. The authentication may first include an age verification before an authentication allows for operation of the device. The authentication may include a control signal communication to the device. The control signal communication may include an audio signal, such as an authentication tone that is detected by a microphone or pressure sensor on the device. The control signal communication may include a
(Continued)

visual, optical, or light signal that is detected by a light sensor or photodiode on the device.

22 Claims, 15 Drawing Sheets

Related U.S. Application Data continuation of application No. 16/441,937, filed on Jun. 14, 2019, now Pat. No. 11,200,770.

(60) Provisional application No. 62/828,222, filed on Apr. 2, 2019.

(56) References Cited

U.S. PATENT DOCUMENTS

| | | | |
|---|---|---|---|
| 11,200,770 | B2 | 12/2021 | Hubbard et al. |
| 11,935,350 | B2 | 3/2024 | Hubbard |
| 2003/0218533 | A1 | 11/2003 | Flick |
| 2003/0230124 | A1 | 12/2003 | Johnson |
| 2009/0126745 | A1 | 5/2009 | Hon |
| 2010/0234987 | A1 | 9/2010 | Benschop et al. |
| 2011/0036346 | A1 | 2/2011 | Cohen et al. |
| 2012/0025950 | A1 | 2/2012 | Von Tippelskirch |
| 2013/0220315 | A1 | 8/2013 | Conley |
| 2014/0096782 | A1 | 4/2014 | Ampolini et al. |
| 2015/0075545 | A1 | 3/2015 | Xiang |
| 2015/0076225 | A1 | 3/2015 | Sweeney |
| 2015/0136158 | A1 | 5/2015 | Stevens et al. |
| 2015/0181945 | A1* | 7/2015 | Tremblay ............... A24F 40/60 131/328 |
| 2015/0196057 | A1 | 7/2015 | Wu |
| 2016/0143361 | A1 | 5/2016 | Juster et al. |
| 2017/0103595 | A1 | 4/2017 | Taylor et al. |
| 2017/0103647 | A1 | 4/2017 | Davis |
| 2018/0020720 | A1 | 1/2018 | Matischek et al. |
| 2018/0093054 | A1 | 4/2018 | Bowen et al. |
| 2018/0289074 | A1 | 10/2018 | Tremblay |
| 2018/0307883 | A1 | 10/2018 | Ebrahimi |
| 2019/0066417 | A1 | 2/2019 | Wang et al. |
| 2019/0095665 | A1 | 3/2019 | Sweeney et al. |
| 2019/0197225 | A1 | 6/2019 | Khalifa et al. |
| 2021/0011446 | A1* | 1/2021 | Anderson ............ G05B 19/042 |
| 2021/0401061 | A1* | 12/2021 | Davis .................. A24F 40/57 |

FOREIGN PATENT DOCUMENTS

| | | |
|---|---|---|
| CN | 106072774 A | 11/2016 |
| CN | 109288138 A | 2/2019 |
| GB | 2522395 A | 7/2015 |
| JP | 07222258 A | 8/1995 |
| JP | H7-222258 | 8/1995 |
| JP | 2005149232 A | 6/2005 |
| JP | 2007013480 A | 1/2007 |
| JP | 2007172605 A | 7/2007 |
| JP | 2007243256 A | 9/2007 |
| JP | 2010141720 A | 6/2010 |
| JP | 2011170438 A | 9/2011 |
| JP | 2014052686 A | 3/2014 |
| JP | 2016148969 A | 8/2016 |
| JP | 2017050739 A1 | 3/2017 |
| JP | 2017208780 A | 11/2017 |
| JP | 2018101235 A | 6/2018 |
| JP | 2019500687 A | 1/2019 |
| JP | 2019502279 A | 1/2019 |
| RU | 2560821 C2 | 8/2015 |
| RU | 2678437 C1 | 1/2019 |
| WO | 2017205692 A1 | 11/2017 |

OTHER PUBLICATIONS

Office Action (with translation) issued in corresponding Korean Application No. 10-2021-7035626 on Jul. 19, 2022, all enclosed pages cited.

Japanese Office Action issued in corresponding Japanese Application No. 2021-560175 on May 10, 2022, all enclosed pages cited.

Chinese Office Action issued in corresponding Chinese Application No. 202080039343.2 on May 11, 2022, all enclosed pages cited.

Office Action (with translation) issued in corresponding Chilean Application No. 2514-2021 on Dec. 20, 2022, all enclosed pages cited.

Office Action issued in corresponding European Application No. 20727743.5 on Dec. 21, 2022, all enclosed pages cited.

Office Action (with translation) issued in corresponding Russian Application No. 2021131895 on Aug. 5, 2022, all enclosed pages cited.

Office Action (with translation) issued in corresponding Japanese Application No. 2021-560475 on Aug. 30, 2022, all enclosed pages cited.

Office Action (with translation) issued in corresponding Saudi Arabian Application No. 521430491 on Sep. 4, 2022, all enclosed pages cited.

Second Office Action (with translation) issued in corresponding Chinese Application No. 202080039343.2 on Nov. 21, 2022, all enclosed pages cited.

Office Action (with translation) issued in corresponding Saudi Arabian Application No. 521430492 on Mar. 27, 2023, all enclosed pages cited.

Decision of Rejection issued in corresponding Chinese Application No. 202080039343.2 on Apr. 18, 2023, all enclosed pages cited.

Office Action issued in corresponding European Application No. 20727743.5 on Jun. 29, 2023, all enclosed pages cited.

Office Action (with translation) issued in corresponding Taiwanese Application No. 109111176 on Jul. 31, 2023, all enclosed pages cited.

Office Action from Canadian Application No. 3135791, dated Nov. 18, 2021, all enclosed pages cited.

Office Action (with translation) issued in corresponding Korean Application No. 10-2023-7005742 on Oct. 18, 2023, all enclosed pages cited.

Office Action (with translation) issued in corresponding Brazilian Application No. BR112021019829-6 on Nov. 14, 2023, all enclosed pages cited.

Office Action (with translation) issued in corresponding Brazilian Application No. BR112021019879-2 on Nov. 14, 2023, all enclosed pages cited.

Office Action (with translation) issued in corresponding Chinese Application No. 202080039419.1 on Dec. 27, 2023, all enclosed pages cited.

Office Action (with translation) issued in corresponding Israeli Application No. 286851 on Dec. 18, 2023, all enclosed pages cited.

Notice of Allowance issued in corresponding European Application No. 20727743.5 on Jan. 23, 2024, all enclosed pages cited.

Office Action (with translation) issued in corresponding Russian Application No. 2021131892 on Sep. 26, 2023, all enclosed pages cited.

Office Action (with translation) issued in corresponding Indonesian Application No. P00202109484 on Nov. 13, 2023, all enclosed pages cited.

Office Action (with translation) issued in corresponding Taiwanese Application No. 109111175 on Oct. 12, 2023, all enclosed pages cited.

Notice of Allowance with English translation issued in corresponding Korean Patent Application No. 10-2023-7005742 mailed Jul. 29, 2024, all pages cited in its entirety.

Office Action issued in corresponding New Zealand Application No. 780511 on Jun. 25, 2024, all enclosed pages cited.

Office Action issued in corresponding New Zealand Application No. 780525 on Jun. 25, 2024, all enclosed pages cited.

Office Action issued in corresponding Canadian Application No. 3,184,325 on May 10, 2024, all enclosed pages cited.

Notification of Reasons for Refusal issued in corresponding Japanese Application No. 2021-560486 on May 21, 2024, all enclosed pages cited.

(56) References Cited

OTHER PUBLICATIONS

Notification of Reasons for Refusal issued in corresponding Japanese Application No. 2022-204194 on Apr. 30, 2024, all enclosed pages cited.
Notification of Grounds for Refusal in corresponding Korean Application No. 10-2024-7036149 dated Dec. 24, 2024.

* cited by examiner

Figure 5

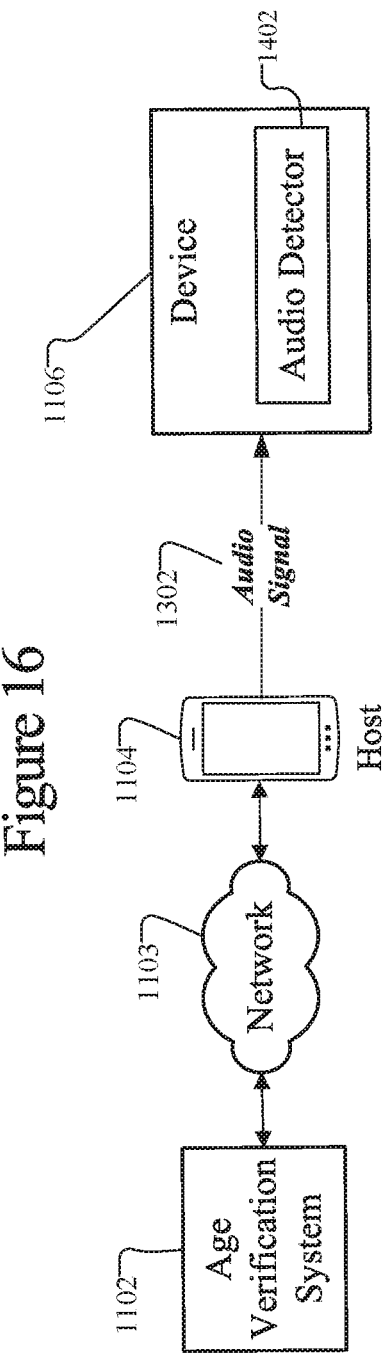
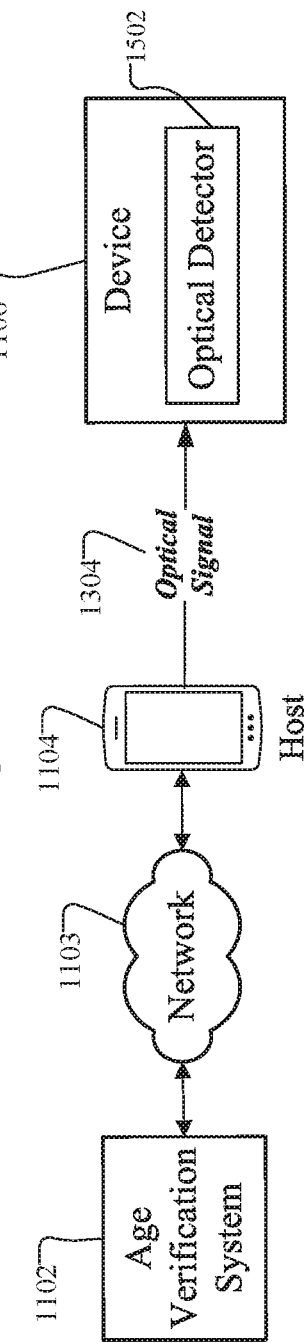

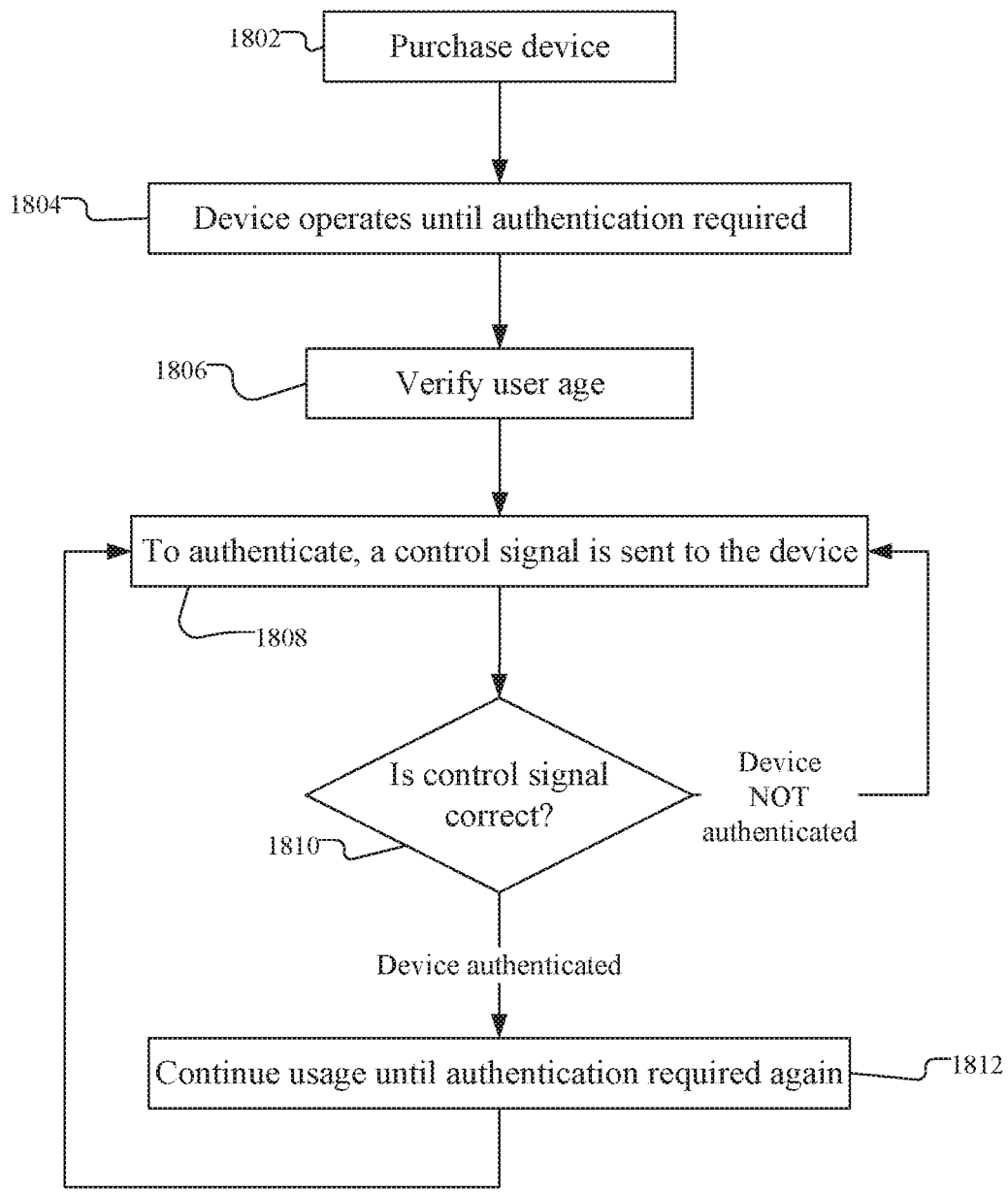

FUNCTIONAL CONTROL AND AGE VERIFICATION OF ELECTRONIC DEVICES THROUGH VISUAL COMMUNICATION

CROSS-REFERENCE TO RELATED APPLICATIONS

This application is a continuation of U.S. patent application Ser. No. 17/548,415 filed Dec. 10, 2021, which is a continuation of U.S. patent application Ser. No. 16/441,937 filed on Jun. 14, 2019, now issued as U.S. Pat. No. 11,200,770, which claims priority to U.S. Provisional Application No. 62/828,222 filed on Apr. 2, 2019; and is related to U.S. patent application Ser. No. 16/441,903, filed on Jun. 14, 2019, the entire contents of each are hereby incorporated by reference in their entirety.

TECHNOLOGICAL FIELD

The present disclosure relates to age verification and control of an aerosol delivery device, such as an electronic nicotine delivery systems ("ENDS") device. The aerosol delivery device is controlled by communication to the device based on the age verification. The communication may include an audio signal or a visual/optical signal, which are provided to authenticate and unlock the device.

BACKGROUND

Many devices have been proposed through the years as improvements upon, or alternatives to, smoking products that require combusting tobacco for use. Some example alternatives have included devices wherein a solid or liquid fuel is combusted to transfer heat to tobacco or wherein a chemical reaction is used to provide such heat source. Additional example alternatives use electrical energy to heat tobacco and/or other aerosol generating substrate materials, such as described in U.S. Pat. No. 9,078,473 to Worm et al., which is incorporated herein by reference. Generally, a device using electrical energy to heat tobacco or other substances may be referred to as an aerosol delivery device and an electronic nicotine delivery systems ("ENDS") device is one example of such a device.

Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous alternative smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 8,881,737 to Collett et al., U.S. Pat. App. Pub. No. 2013/0255702 to Griffith Jr. et al., U.S. Pat. App. Pub. No. 2014/0000638 to Sebastian et al., U.S. Pat. App. Pub. No. 2014/0096781 to Sears et al., U.S. Pat. App. Pub. No. 2014/0096782 to Ampolini et al., U.S. Pat. App. Pub. No. 2015/0059780 to Davis et al., and U.S. patent application Ser. No. 15/222,615 to Watson et al., filed Jul. 28, 2016, all of which are incorporated herein by reference. See also, for example, the various implementations of products and heating configurations described in the background sections of U.S. Pat. No. 5,388,594 to Counts et al. and U.S. Pat. No. 8,079,371 to Robinson et al., which are incorporated by reference.

The smoking articles described above may be subject to certain restrictions, including age restrictions. In some locations, use of the articles including the cartridges of an ENDS device is limited based on user age. An improved process for the authentication of a device by an age verified user may be needed.

BRIEF SUMMARY

The present disclosure relates to controlling an aerosol delivery device, including an electronic nicotine delivery systems ("ENDS") device. The ENDS or aerosol delivery devices may operate when authenticated. The authentication may first include an age verification before an authentication allows for operation of the device. The authentication may include a control signal communication to the device. The control signal communication may include an audio signal, such as an authentication tone that is detected by a microphone or pressure sensor on the device. The control signal communication may include a visual, optical, or light signal that is detected by a light sensor or photodiode on the device. The audio or visual signal may be sent by a host device (e.g. smartphone), based on a help desk phone call, or be from a point of sale location.

In one embodiment, a system comprises an age verification system configured to verify an age of a user, a host device configured to communicate with the age verification system and configured to transmit an audio signal based on the verification of the user, and an aerosol delivery device configured to be authenticated in response to receipt and confirmation of the audio signal from the host device. The aerosol delivery device may further include an audio detector configured to detect the audio signal. The audio detector may include a pressure sensor configured to detect pressure changes caused by the audio signal. The pressure sensor may be configured to measure a difference in pressure caused by a puff on the aerosol delivery device in addition to detecting the audio signal. The measurement of the difference in pressure may be caused by the puff activates a heater in the aerosol delivery device that generates an aerosol for inhalation. The audio detector may further include a microphone configured to detect the audio signal. The microphone may include a MEMS electret microphone using a film diaphragm. The audio signal may be translated to determine if the audio signal is correct for authenticating the aerosol delivery device. The host device may include a computing device with a speaker that transmits the audio signal. The host device may access a user profile for the user for the authentication.

In another embodiment, a method for authenticating an aerosol delivery device includes receiving a request for age verification of a user of the aerosol delivery device, determining the age of the user, performing an age verification based on the determined age of the user, and authenticating, in response to the age verification, the aerosol delivery device for the user. The authenticating comprises transmitting an audio signal for the aerosol delivery device. The receiving a request may include receiving a telephone call from the user. The audio signal may be transmitted through the telephone call to be detected by the aerosol delivery device. The telephone call may be received and answered by a help desk operator. The audio signal may include an authentication tone. The authenticating may include unlocking the aerosol delivery device in response to detection of a correct audio signal.

In another embodiment, an aerosol delivery device includes a power source configured to provide power to generate an aerosol, a signal detector configured to detect an audio signal, and a signal detector circuitry configured to receive the audio signal, translate the audio signal, and authenticate the aerosol delivery device when the audio signal is correct. The signal detector may include a pressure sensor configured to detect pressure changes caused by the audio signal and further configured to measure a difference in pressure caused by a puff on the aerosol delivery device that is used to activate a heater in the aerosol delivery device that generates an aerosol for inhalation. The signal detector may include a microphone configured to detect the audio signal. The audio signal may be translated to determine if the audio signal is correct for authenticating the aerosol delivery device. The audio signal may be received from a speaker of a host device that plays the audio signal for the signal detector. The device may include an aerosol production component coupled with the power source such that the aerosol production component receives power to generate the aerosol. The device may include a canal to the signal detector for the audio signal to travel.

In one embodiment, a system includes an age verification system configured to verify an age of a user, a host device configured to communicate with the age verification system and configured to transmit an optical signal based on the verification of the user, and an aerosol delivery device configured to be authenticated in response to receipt and confirmation of the optical signal from the host device. The aerosol delivery device may include an optical detector configured to detect the optical signal. The optical detector may include a light sensor configured to detect the optical signal. The optical signal may include a series of pulses with one or more of varying wavelengths, brightness, or pulse width, that are detected by the light sensor. The optical detector may include a photodiode configured to detect the optical signal. The host device may be a computing device coupled with a network for communicating with the age verification system. The optical signal may include a sequence of light pulses. The optical signal detected by the optical detector may originate from a flashlight of the computing device or from a display screen of the computing device. The optical signal may be translated to determine if the optical signal is correct for authenticating the aerosol delivery device. The host device may access a user profile for the user for the authentication. An authentication key may modify light from a light source to form the optical signal.

In another embodiment, a method for authenticating an aerosol delivery device includes receiving an age verification request for a user of the aerosol delivery device, verifying an age of the user and providing the age verification, and providing instructions for generating an optical signal to be communicated with the aerosol delivery device when the age of the user is verified. The generating the optical signal includes authenticating the aerosol delivery device. The authenticating may include unlocking the aerosol delivery device in response to detecting a correct optical signal. The optical signal may be generated by a host device that communicates the optical signal to the aerosol delivery device. The host device may communicate with an age verification system. The host device may access a user profile for the user for the authentication. The age verification may include comparing identification documentation.

In another embodiment, an aerosol delivery device includes a power source configured to provide power to generate an aerosol, a signal detector configured to detect an optical signal, and signal detector circuitry configured to receive the video signal, translate the optical signal, and authenticate the aerosol delivery device when the optical signal is correct. The signal detector may include a light sensor or photodiode configured to detect the optical signal. The optical signal may be translated by a translator from the signal detector circuitry to determine if the optical signal is correct for authenticating the aerosol delivery device. The optical signal may be transmitted to the signal detector by a host device that displays the optical signal on a screen of the host device or from a flashlight function of the host device.

It will be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE FIGURES

Figure 1:
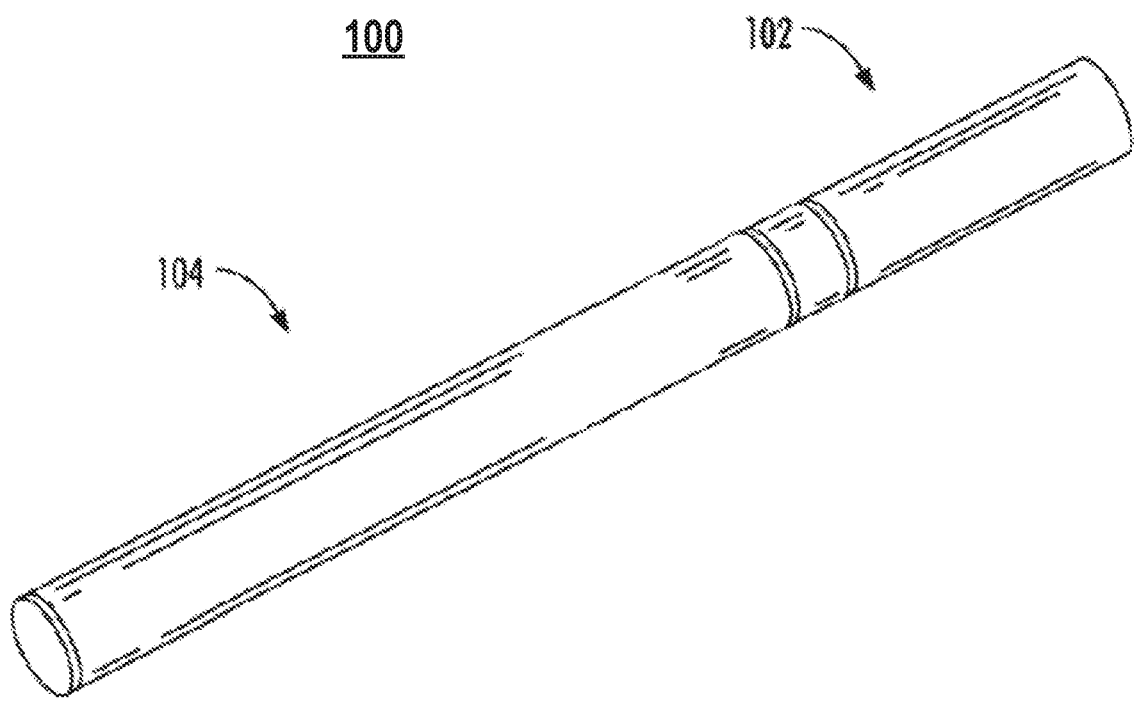

Having thus described aspects of the disclosure in the foregoing general terms, reference will now be made to the accompanying figures, which are not necessarily drawn to scale, and wherein:

FIG. 1 illustrates a perspective view of an aerosol delivery device including a cartridge and a control body that are coupled to one another, according to an example implementation of the present disclosure.

Figure 2:
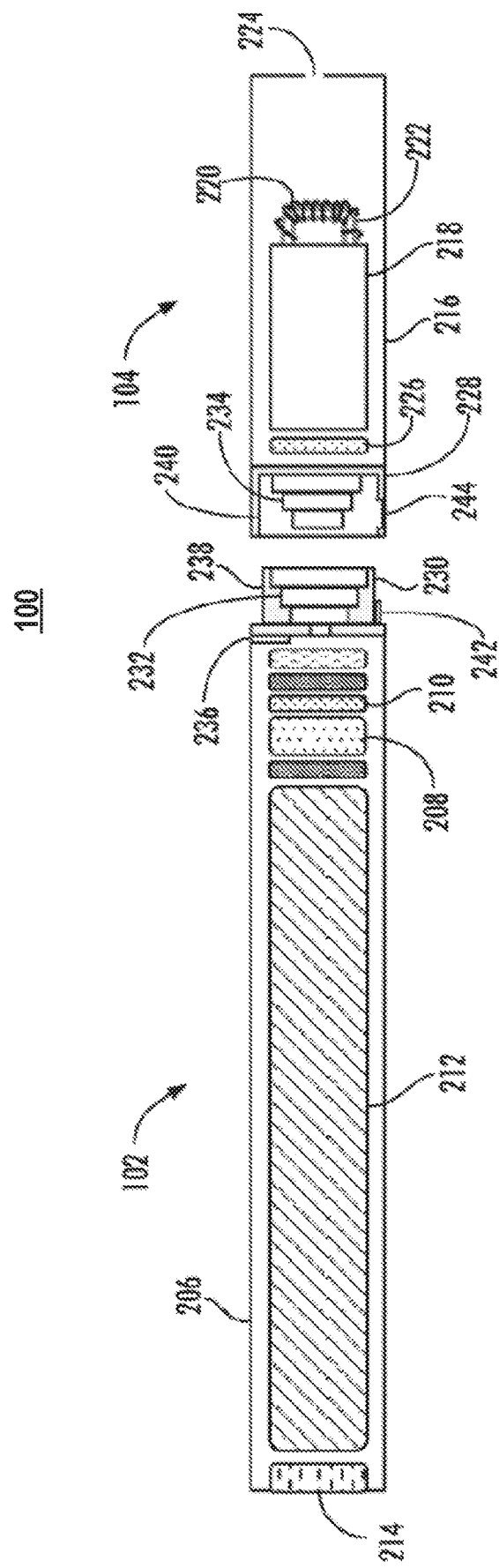

FIG. 2 is a partially cut-away view of the aerosol delivery device of FIG. 1 in which the cartridge and control body are decoupled from one another, according to an example implementation.

Figure 3:
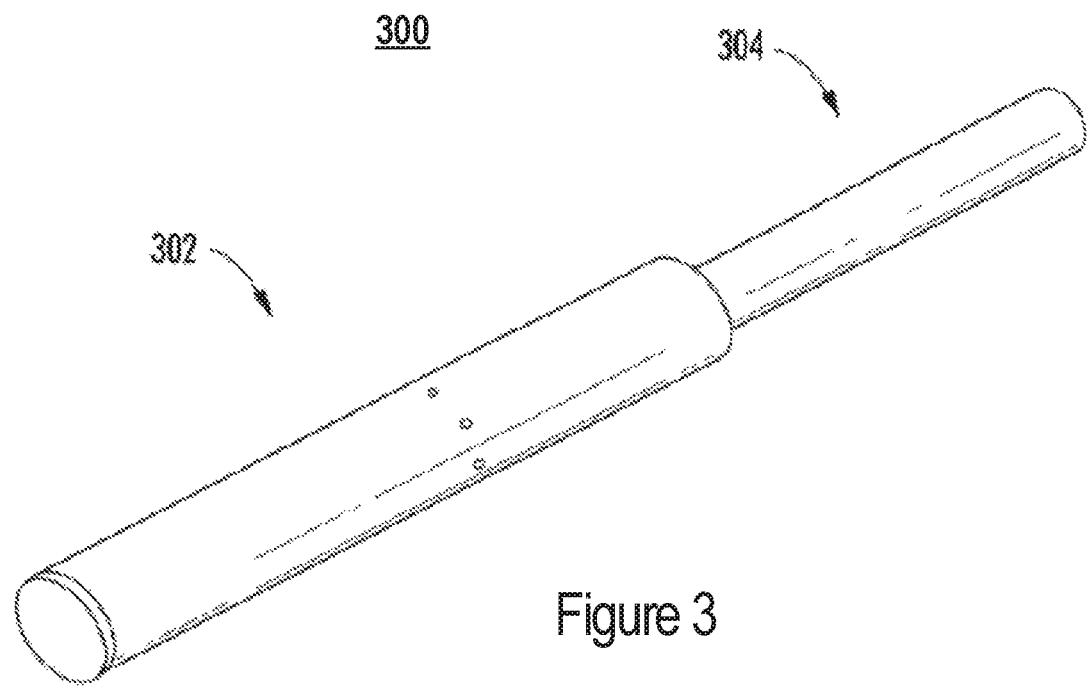
Figure 4:
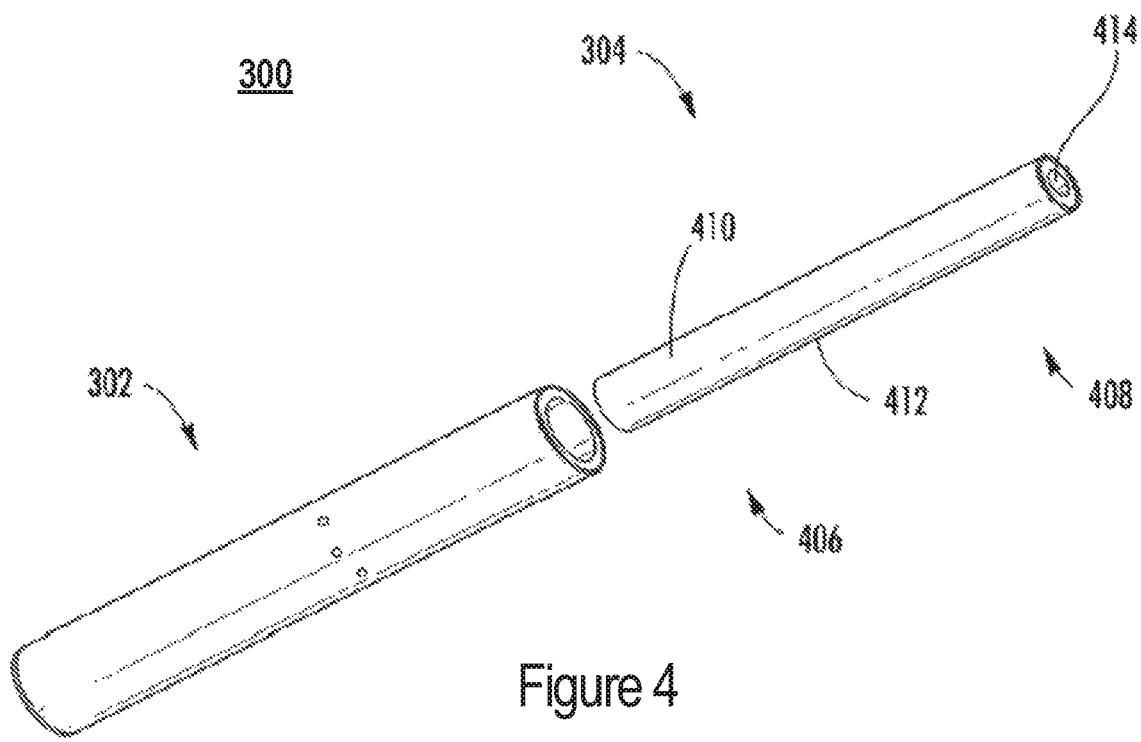

FIGS. 3 and 4 illustrate a perspective view of an aerosol delivery device comprising a control body and an aerosol source member that are respectively coupled to one another and decoupled from one another, according to another example implementation of the present disclosure.

Figure 5:
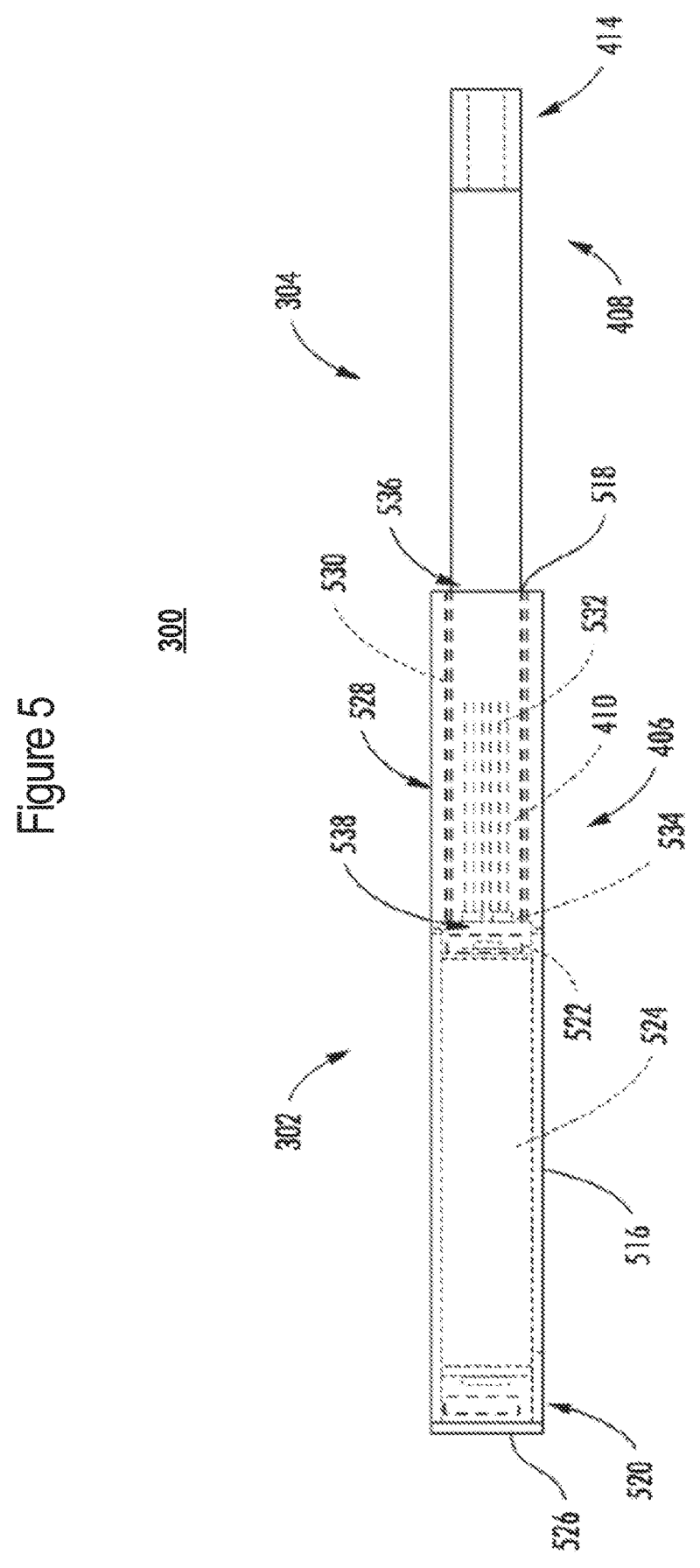
Figure 6:
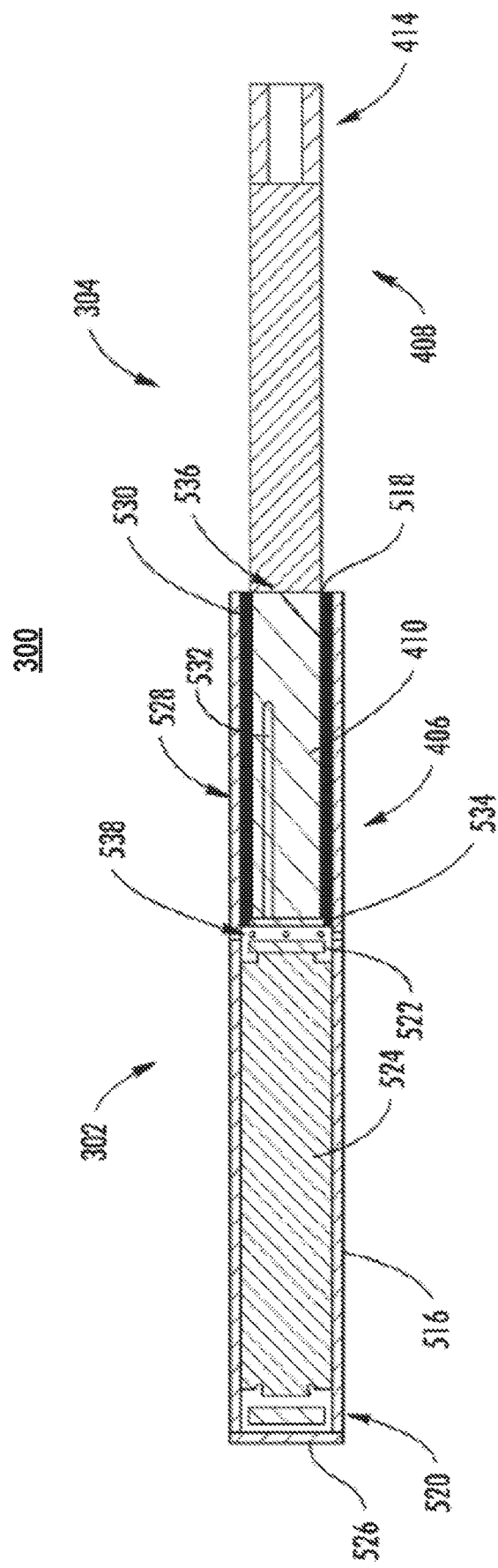

FIGS. 5 and 6 illustrate respectively a front view of and a sectional view through the aerosol delivery device of FIGS. 3 and 4, according to an example implementation.

Figure 7:
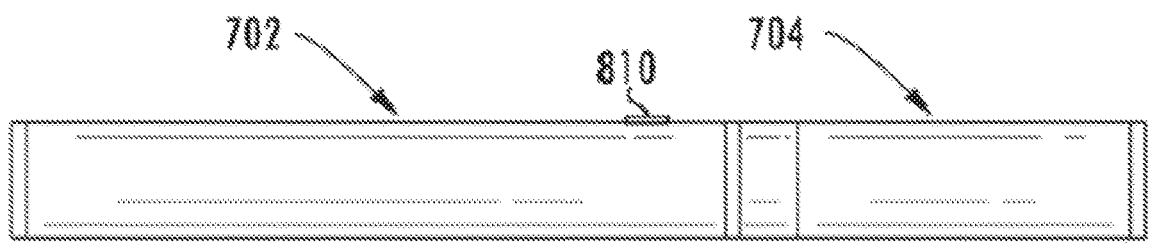
Figure 8:
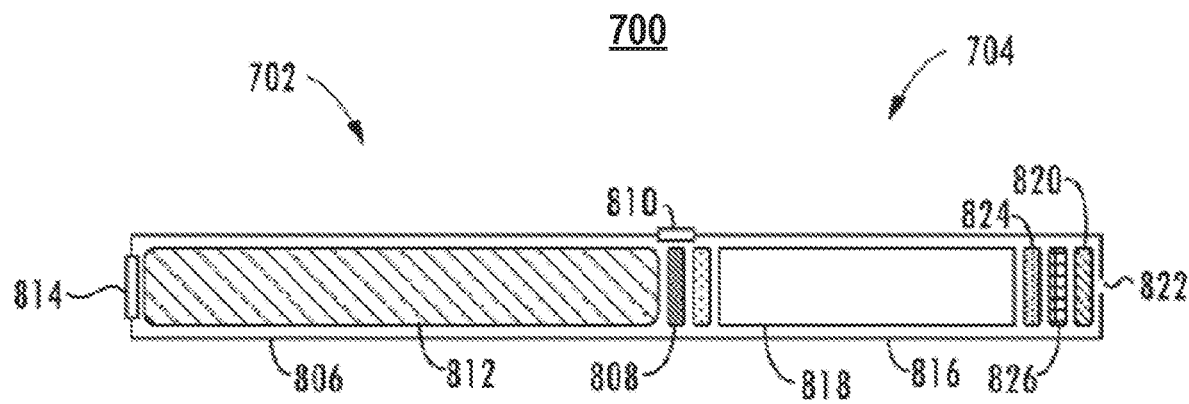

FIGS. 7 and 8 illustrate respectively a side view and a partially cut-away view of an aerosol delivery device including a cartridge coupled to a control body, according to example implementations.

Figure 9:
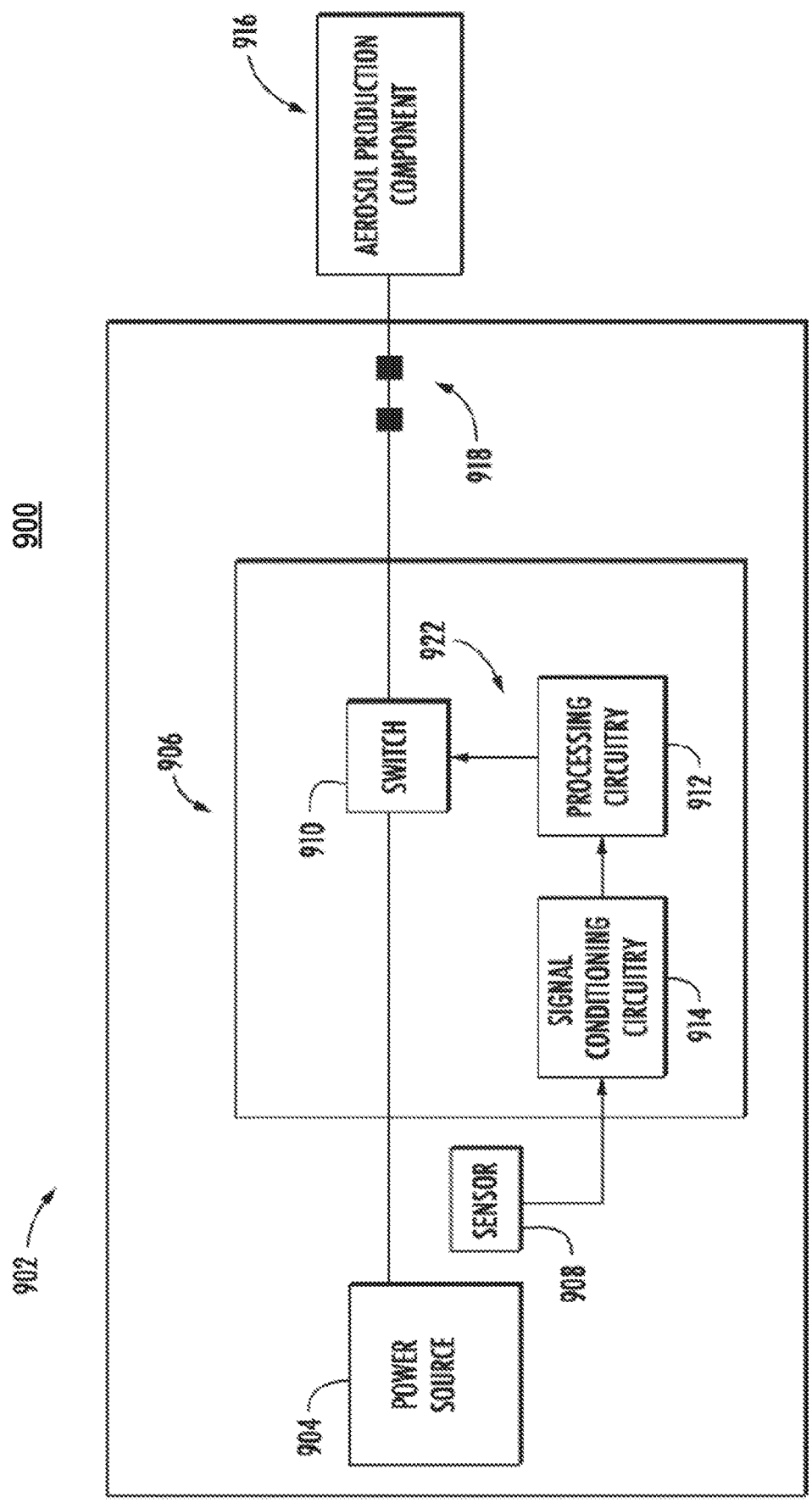

FIG. 9 illustrates a circuit diagram of an aerosol delivery device according to various example implementations of the present disclosure.

Figure 10:
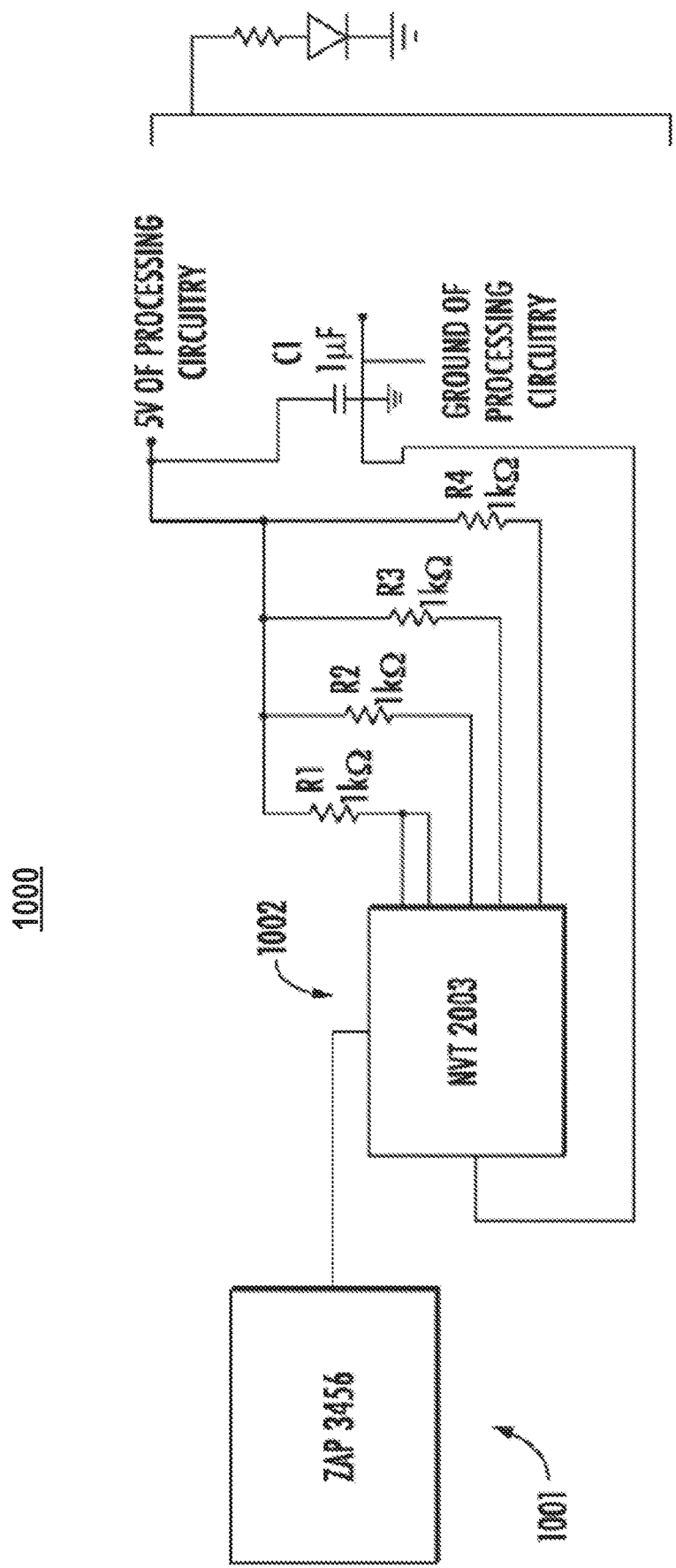

FIG. 10 illustrates a circuit diagram of signal conditioning circuitry according to an example implementation of the present disclosure.

Figure 11:
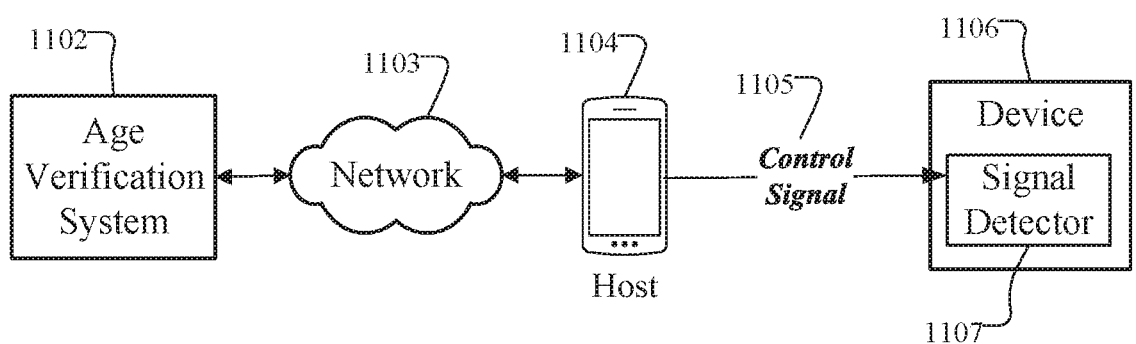

FIG. 11 illustrates an example system diagram for functional control of a device.

Figure 12:
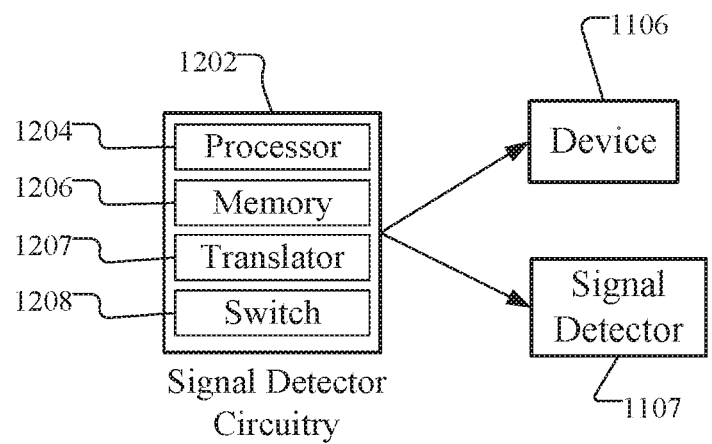

FIG. 12 illustrates an embodiment of signal detector circuitry.

Figure 13:
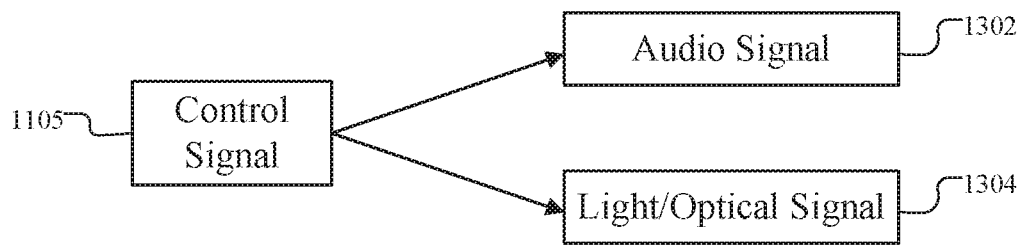

FIG. 13 illustrates embodiments of a control signal.

Figure 14:
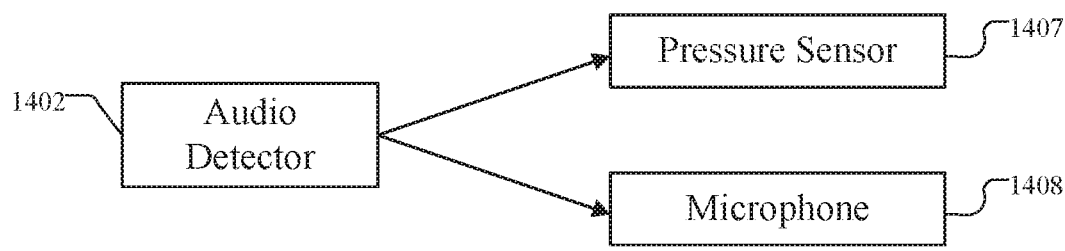

FIG. 14 illustrates embodiments of an audio detector.

Figure 15:
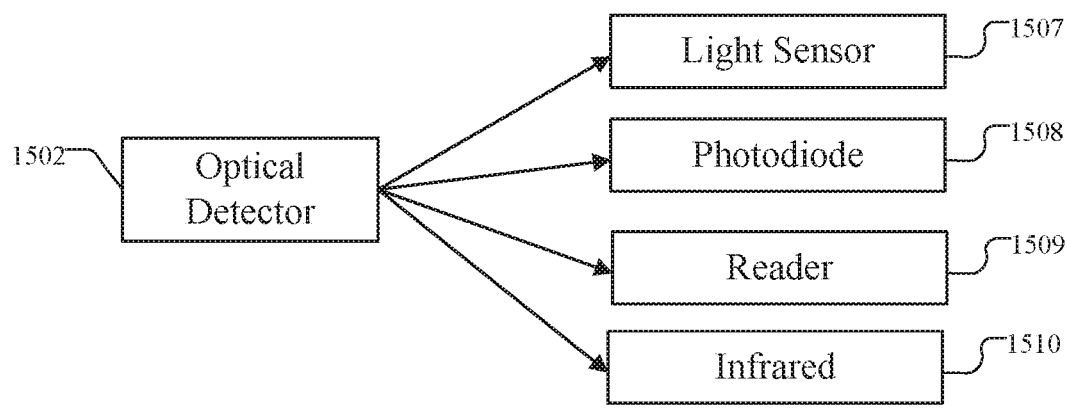

FIG. 15 illustrates embodiments of an optical detector.

FIG. 16 illustrates an example system diagram for functional control of a device with an audio signal.

FIG. 17 illustrates an example system diagram for functional control of a device with an optical signal.

FIG. 18 is a flow chart illustrating one example of the control signal process.

Figure 19:
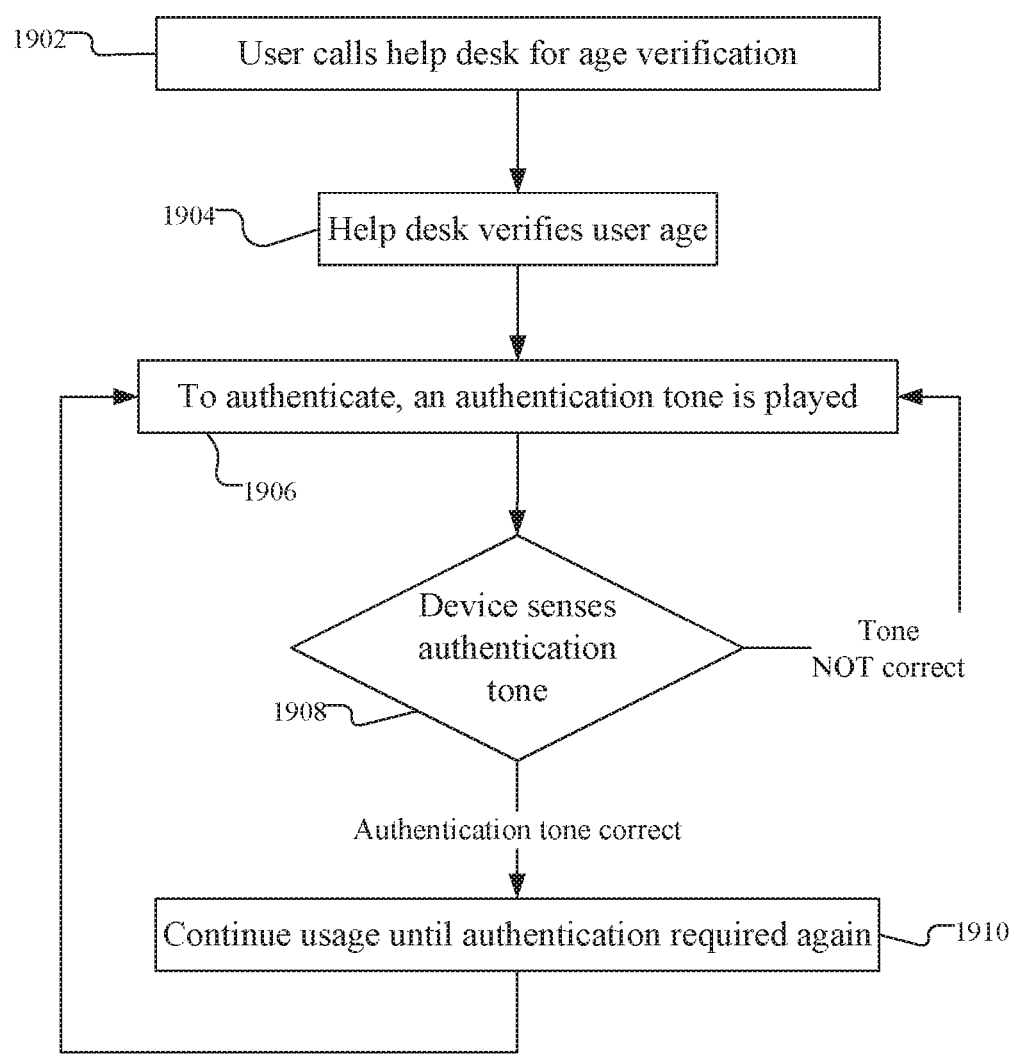

FIG. 19 is a flow chart illustrating one example of the audio signal process.

Figure 20:
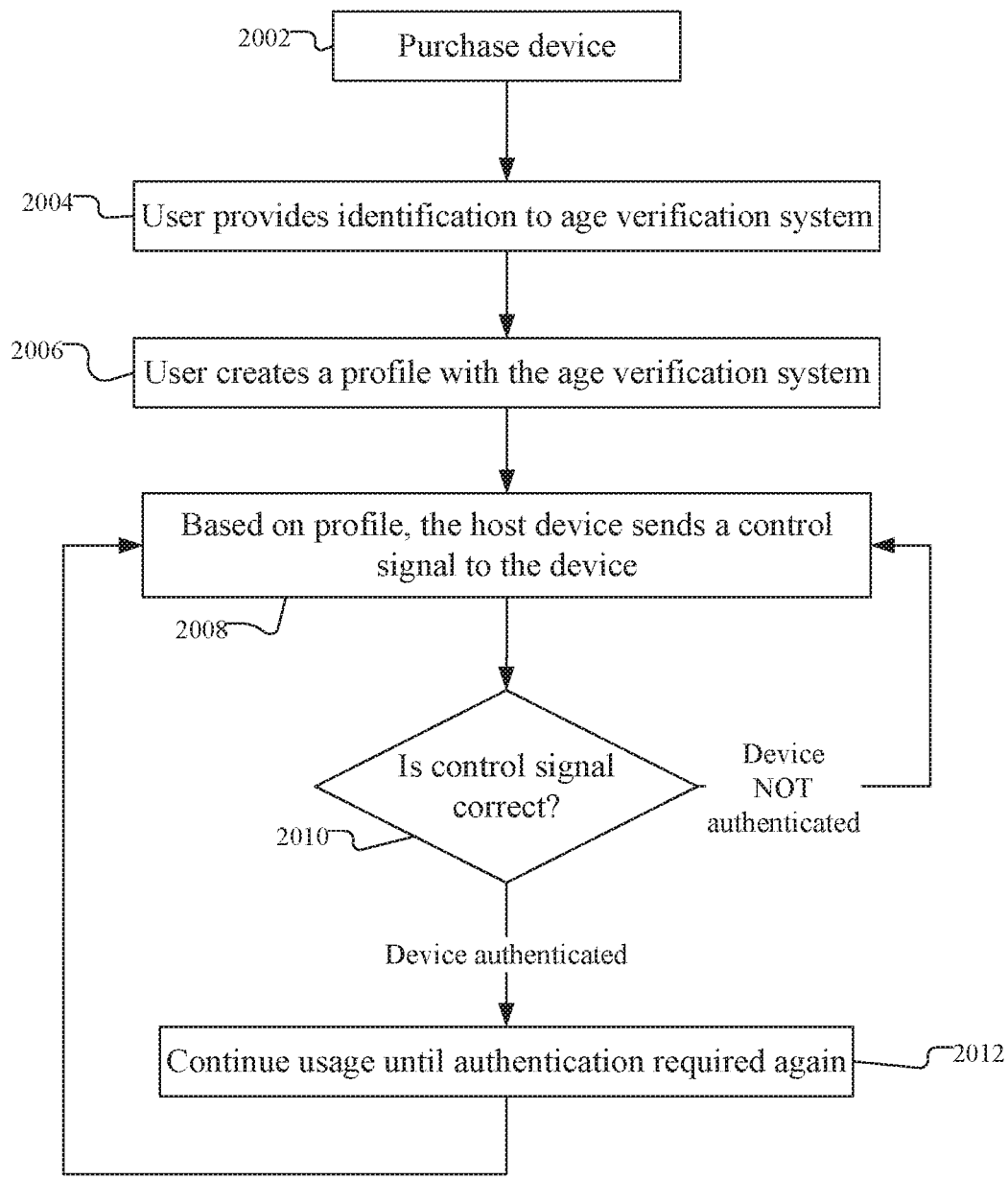

FIG. 20 is a flow chart illustrating one example of authentication with a host device.

Figure 21:
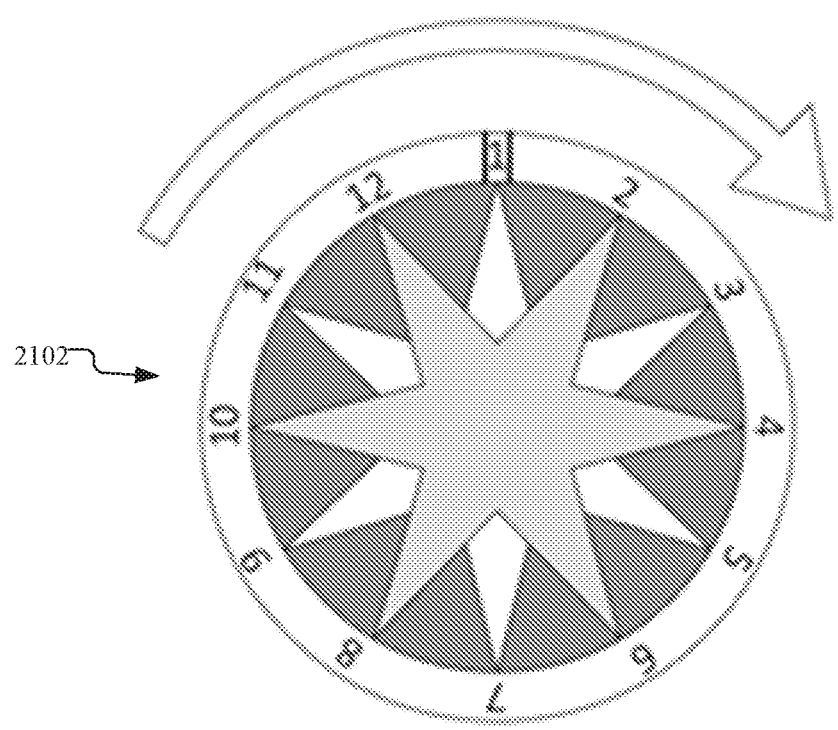

FIG. 21 illustrates an example authentication key.

DETAILED DESCRIPTION

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise. Also, while reference may be made herein to quantitative measures, values, geometric relationships or the like, unless otherwise stated, any one or more if not all of these may be absolute or approximate to account for acceptable variations that may occur, such as those due to engineering tolerances or the like.

As described hereinafter, the present disclosure relates to requiring an authentication of an age-restricted device, such as an aerosol delivery device or an electronic nicotine delivery systems ("ENDS") device. The authentication may include or require a prior age verification, such that the age-restricted device is not operational for a user that is not age-verified. The authentication may include the age-restricted device receiving a control signal for authenticating the device. The control signal may include audio signals and/or visual/optical signals for authenticating the device.

An aerosol delivery device or ENDS are examples of such a device that may be associated with restriction, such as an age restriction. Other examples include delivery devices for delivery of cannabinoids, such as Tetrahydrocannabinol (THC) and/or Cannabidiol (CBD), botanicals, medicinals, and/or other active ingredients. Thus, it will be appreciated that while an aerosol delivery or ENDS device is used as an example application of various embodiments throughout, this example is intended to be non-limiting such that inventive concepts disclosed herein can be used with devices other than aerosol delivery or ENDS devices, including aerosol delivery devices that may be used to deliver other medicinal and/or active ingredients to a user or may include smokeless tobacco or other tobacco products.

The device authentication by a control signal can be in addition to, or may be required as a prerequisite to, the user performing age verification. A user that has not been age verified cannot authenticate a device. The authentication may need to be performed periodically for usage of an age-restricted product. There may be an age verification system for confirming an age of a user and/or authenticating the proper user and/or device.

The functional control and authentication may be applicable to any age restricted device or substance, including nicotine, cigarettes, alcohol, Tetrahydrocannabinol (THC), Cannabidiol (CBD), CBD oil, cannabis/marijuana, botanicals, medicinals, and/or other age restricted products. The authentication may be applicable to age-restricted devices other than an aerosol delivery device. Likewise, although age is one example of a restriction for the device, there may be other types of restrictions on the device that are verified through authentication of the device.

Aerosol delivery devices are one example of a device that may be restricted and authentication may be accomplished with a control signal to the device. Aerosol delivery devices are further described with respect to FIGS. 1-10. In other examples, the device may be a heat-not-burn device using an aerosol source member as a consumable rather than a cartridge. The aerosol delivery devices may be configured to produce an aerosol (an inhalable substance) from an aerosol precursor composition (sometimes referred to as an inhalable substance medium). The aerosol precursor composition may comprise one or more of a solid tobacco material, a semi-solid tobacco material, or a liquid aerosol precursor composition. In some implementations, the aerosol delivery devices may be configured to heat and produce an aerosol from a fluid aerosol precursor composition (e.g., a liquid aerosol precursor composition). Additionally or alternatively, the aerosol precursor composition may comprise one or more substances mentioned above, including but not limited to botanical substances, medicinal substances, alcohol, glycerin, and may include nicotine, and/or other active ingredients including, but not limited to, botanical ingredients (e.g., lavender, peppermint, chamomile, basil, rosemary, thyme, eucalyptus, ginger, cannabis, ginseng, maca, and tisanes), stimulants (e.g., caffeine and guarana), amino acids (e.g., taurine, theanine, phenylalanine, tyrosine, and tryptophan) and/or pharmaceutical, nutraceutical, and medicinal ingredients (e.g., vitamins, such as B6, B12, and C and cannabinoids, such as tetrahydrocannabinol (THC) and cannabidiol (CBD)). Such aerosol delivery devices may include so-called electronic cigarettes. In other implementations, the aerosol delivery devices may comprise heat-not-burn devices. In yet other implementations, the aerosol delivery devices may comprise no-heat-no-burn devices.

Liquid aerosol precursor composition, also referred to as a vapor precursor composition or "e-liquid," is particularly useful for electronic cigarettes and no-heat-no-burn devices. Liquid aerosol precursor composition may comprise a variety of components including, by way of example, a polyhydric alcohol (e.g., glycerin, propylene glycol, or a mixture thereof), nicotine, tobacco, tobacco extract, and/or flavorants. In some examples, the aerosol precursor composition comprises glycerin and nicotine. In other examples, the composition may additionally or alternatively include alcohol, botanical ingredients (e.g., lavender, peppermint, chamomile, basil, rosemary, thyme, eucalyptus, ginger, cannabis, ginseng, maca, and tisanes), stimulants (e.g., caffeine and guarana), amino acids (e.g., taurine, theanine, phenylalanine, tyrosine, and tryptophan), pharmaceutical, nutraceutical, and medicinal ingredients (e.g., vitamins, such as B6, B12, and C and cannabinoids, such as tetrahydrocannabinol (THC) and cannabidiol (CBD)), or other active ingredients, or some combination thereof.

Some liquid aerosol precursor compositions that may be used in conjunction with various implementations may include one or more acids such as levulinic acid, succinic acid, lactic acid, pyruvic acid, benzoic acid, fumaric acid, combinations thereof, and the like. Inclusion of an acid(s) in liquid aerosol precursor compositions including nicotine may provide a protonated liquid aerosol precursor composition, including nicotine in salt form. Representative types of liquid aerosol precursor components and formulations are set forth and characterized in U.S. Pat. No. 7,726,320 to Robinson et al.; U.S. Pat. No. 9,254,002 to Chong et al.; and U.S. Pat. App. Pub. Nos. 2013/0008457 to Zheng et al., 2015/0020823 to Lipowicz et al., and 2015/0020830 to Koller; as well as PCT Pat. App. Pub. No. WO 2014/182736 to Bowen et al.; and U.S. Pat. No. 8,881,737 to Collett et al., the disclosures of which are incorporated herein by reference. Other aerosol precursors that may be employed include the aerosol precursors that have been incorporated in any of a number of the representative products identified above. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN. Implementations of effervescent materials can be used with the aerosol precursor, and are described, by way of example, in U.S. Pat. App. Pub. No. 2012/0055494 to Hunt et al., which is incorporated herein by reference. Further, the use of effervescent materials is described, for example, in U.S. Pat. No. 4,639,368 to Niazi et al.; U.S. Pat. No. 5,178,878 to Wehling et al.; U.S. Pat. No. 5,223,264 to Wehling et al.; U.S. Pat. No. 6,974,590 to Pather et al.; U.S. Pat. No. 7,381,667 to Bergquist et al.; U.S. Pat. No. 8,424,541 to Crawford et al.; U.S. Pat. No. 8,627,828 to Strickland et al.; and U.S. Pat. No. 9,307,787 to Sun et al.; as well as U.S. Pat. App. Pub. Nos. 2010/0018539 to Brinkley et al., and PCT Pat. App. Pub. No. WO 97/06786 to Johnson et al., all of which are incorporated by reference herein.

Representative types of substrates, reservoirs or other components for supporting the aerosol precursor are described in U.S. Pat. No. 8,528,569 to Newton; U.S. Pat. App. Pub. No. 2014/0261487 to Chapman et al.; U.S. Pat. App. Pub. No. 2015/0059780 to Davis et al.; and U.S. Pat. App. Pub. No. 2015/0216232 to Bless et al., all of which are incorporated herein by reference. Additionally, various wicking materials, and the configuration and operation of those wicking materials within certain types of electronic cigarettes, are set forth in U.S. Pat. No. 8,910,640 to Sears et al., which is incorporated herein by reference.

In other implementations, the aerosol delivery devices may comprise heat-not-burn devices, configured to heat a solid aerosol precursor composition (e.g., an extruded tobacco rod) or a semi-solid aerosol precursor composition (e.g., a glycerin-loaded tobacco paste). The aerosol precursor composition may comprise tobacco-containing beads, tobacco shreds, tobacco strips, reconstituted tobacco material, or combinations thereof, and/or a mix of finely ground tobacco, tobacco extract, spray dried tobacco extract, or other tobacco form mixed with optional inorganic materials (such as calcium carbonate), optional flavors, and aerosol forming materials to form a substantially solid or moldable (e.g., extrudable) substrate. Representative types of solid and semi-solid aerosol precursor compositions and formulations are disclosed in U.S. Pat. No. 8,424,538 to Thomas et al.; U.S. Pat. No. 8,464,726 to Sebastian et al.; U.S. Pat. App. Pub. No. 2015/0083150 to Conner et al.; U.S. Pat. App. Pub. No. 2015/0157052 to Ademe et al.; and U.S. Pat. App. Pub. No. 2017/0000188 to Nordskog et al., all of which are incorporated by reference herein. Further representative types of solid and semi-solid aerosol precursor compositions and arrangements include those found in the NEOSTIKS™ consumable aerosol source members for the GLO™ product by British American Tobacco and in the HEETS™ consumable aerosol source members for the IQOS™ product by Philip Morris International, Inc.

In various implementations, the inhalable substance specifically may be a tobacco component or a tobacco-derived material (i.e., a material that is found naturally in tobacco that may be isolated directly from the tobacco or synthetically prepared). For example, the aerosol precursor composition may comprise tobacco extracts or fractions thereof combined with an inert substrate. The aerosol precursor composition may further comprise unburned tobacco or a composition containing unburned tobacco that, when heated to a temperature below its combustion temperature, releases an inhalable substance. In some implementations, the aerosol precursor composition may comprise tobacco condensates or fractions thereof (i.e., condensed components of the smoke produced by the combustion of tobacco, leaving flavors and, possibly, nicotine).

In other implementations, smokeless tobacco and other tobacco products may be examples of an age-restricted product rather than an aerosol delivery or ENDS device. Representative smokeless tobacco products that have been marketed may include those referred to as CAMEL Snus, CAMEL Orbs, CAMEL Strips, and CAMEL Sticks by R. J. Reynolds Tobacco Company; GRIZZLY moist tobacco, KODIAK moist tobacco, LEVI GARRETT loose tobacco and TAYLOR'S PRIDE loose tobacco by American Snuff Company, LLC; KAYAK moist snuff and CHATTANOOGA CHEW chewing tobacco by Swisher International, Inc.; REDMAN chewing tobacco by Pinkerton Tobacco Co. LP; COPENHAGEN moist tobacco, COPENHAGEN Pouches, SKOAL Bandits, SKOAL Pouches, RED SEAL long cut and REVEL Mint Tobacco Packs by U.S. Smokeless Tobacco Company; and MARLBORO Snus and Taboka by Philip Morris USA. Representative types of snuff products, commonly referred to as "snus," may be manufactured in Europe, particularly in Sweden, by or through companies such as Swedish Match AB, Fiedler & Lundgren AB, Gustavus AB, Skandinavisk Tobakskompagni A/S and Rocker Production AB. Snus products previously or currently available in the U.S.A. have been marketed under the trade names such as CAMEL Snus Frost, CAMEL Snus Original, and CAMEL Snus Spice, CAMEL Snus Mint, CAMEL Snus Mellow, CAMEL Snus Winterchill, and CAMEL Snus Robust by R. J. Reynolds Tobacco Company. Smokeless tobacco products have been packaged in tins, "pucks" or "pots." Other example products include nicotine lozenges, such as REVEL nicotine lozenges (R. J. Reynolds Vapor Company product), and tobacco-free nicotine pouched products, such as Zyn by Swedish Match and LYFT.

Tobacco materials useful in the present disclosure can vary and may include, for example, flue-cured tobacco, burley tobacco, Oriental tobacco or Maryland tobacco, dark tobacco, dark-fired tobacco and Rustica tobaccos, as well as other rare or specialty tobaccos, or blends thereof. Tobacco materials also can include so-called "blended" forms and processed forms, such as processed tobacco stems (e.g., cut-rolled or cut-puffed stems), volume expanded tobacco (e.g., puffed tobacco, such as dry ice expanded tobacco (DIET), preferably in cut filler form), reconstituted tobaccos (e.g., reconstituted tobaccos manufactured using paper-making type or cast sheet type processes). Various representative tobacco types, processed types of tobaccos, and types of tobacco blends are set forth in U.S. Pat. No. 4,836,224 to Lawson et al., U.S. Pat. No. 4,924,888 to Perfetti et al., U.S.

Pat. No. 5,056,537 to Brown et al., U.S. Pat. No. 5,159,942 to Brinkley et al., U.S. Pat. No. 5,220,930 to Gentry, U.S. Pat. No. 5,360,023 to Blakley et al., U.S. Pat. No. 6,701,936 to Shafer et al., U.S. Pat. No. 7,011,096 to Li et al., U.S. Pat. No. 7,017,585 to Li et al., and U.S. Pat. No. 7,025,066 to Lawson et al.; U.S. Pat. App. Pub. No. 2004/0255965 to Perfetti et al.; PCT Pat. App. Pub. No. WO 02/37990 to Bereman; and Bombick et al., Fund. Appl. Toxicol., 39, p. 11-17 (1997), which are incorporated herein by reference. Further example tobacco compositions that may be useful in a smoking device, including according to the present disclosure, are disclosed in U.S. Pat. No. 7,726,320 to Robinson et al., which is incorporated herein by reference.

Still further, the aerosol precursor composition may comprise an inert substrate having the inhalable substance, or a precursor thereof, integrated therein or otherwise deposited thereon. For example, a liquid comprising the inhalable substance may be coated on or absorbed or adsorbed into the inert substrate such that, upon application of heat, the inhalable substance is released in a form that can be withdrawn from the inventive article through application of positive or negative pressure. In some aspects, the aerosol precursor composition may comprise a blend of flavorful and aromatic tobaccos in cut filler form. In another aspect, the aerosol precursor composition may comprise a reconstituted tobacco material, such as described in U.S. Pat. No. 4,807,809 to Pryor et al.; U.S. Pat. No. 4,889,143 to Pryor et al.; and U.S. Pat. No. 5,025,814 to Raker, the disclosures of which are incorporated herein by reference. For further information regarding suitable aerosol precursor composition, see U.S. patent application Ser. No. 15/916,834 to Sur et al., filed Mar. 9, 2018, which is incorporated herein by reference.

Regardless of the type of aerosol precursor composition, aerosol delivery devices may include an aerosol production component configured to produce an aerosol from the aerosol precursor composition. In the case of an electronic cigarette or a heat-not-burn device, for example, the aerosol production component may be or include a heating element. In the case of a no-heat-no-burn device, in some examples, the aerosol production component may be or include a vibratable piezoelectric or piezomagnetic mesh. In other words, there may not be a heating element for aerosol production. The aerosol delivery device of some embodiments may include a combination of elements to provide the aerosol production component, which can include both a heating element and an additional element, such as a vibrating aerosol production component (e.g., a vibratable piezoceramic and/or other piezoelectric or piezomagnetic material) that cooperate to produce aerosol from an aerosol precursor composition.

One example of a suitable heating element is an induction heater. Such heaters often comprise an induction transmitter and an induction receiver. The induction transmitter may include a coil configured to create an oscillating magnetic field (e.g., a magnetic field that varies periodically with time) when alternating current is directed through it. The induction receiver may be at least partially located or received within the induction transmitter and may include a conductive material (e.g., ferromagnetic material or an aluminum coated material). By directing alternating current through the induction transmitter, eddy currents may be generated in the induction receiver via induction. The eddy currents flowing through the resistance of the material defining the induction receiver may heat it by Joule heating (i.e., through the Joule effect). The induction receiver, which may define an atomizer, may be wirelessly heated to form an aerosol from an aerosol precursor composition positioned in proximity to the induction receiver. Various implementations of an aerosol delivery device with an induction heater are described in U.S. Pat. App. Pub. No. 2017/0127722 to Davis et al.; U.S. Pat. App. Pub. No. 2017/0202266 to Sur et al.; U.S. patent application Ser. No. 15/352,153 to Sur et al., filed Nov. 15, 2016; U.S. patent application Ser. No. 15/799,365 to Sebastian et al., filed Oct. 31, 2017; and U.S. patent application Ser. No. 15/836,086 to Sur, all of which are incorporated by reference herein.

In other implementations including those described more particularly herein, the heating element is a conductive heater such as in the case of electrical resistance heater. These heaters may be configured to produce heat when an electrical current is directed through it. In various implementations, a conductive heater may be provided in a variety forms, such as in the form of a foil, a foam, discs, spirals, fibers, wires, films, yarns, strips, ribbons or cylinders. Such heaters often include a metal material and are configured to produce heat as a result of the electrical resistance associated with passing an electrical current through it. Such resistive heaters may be positioned in proximity to and heat an aerosol precursor composition to produce an aerosol. A variety of conductive substrates that may be usable with the present disclosure are described in the above-cited U.S. Pat. App. Pub. No. 2013/0255702 to Griffith et al.

In some implementations aerosol delivery devices may include a control body and a cartridge in the case of so-called electronic cigarettes or no-heat-no-burn devices, or a control body and an aerosol source member in the case of heat-not-burn devices. The cartridge may be one example of a consumable for a device and the reference to a cartridge may include other consumables. Other examples of an aerosol source member, may include a "stick" such as may contain tobacco, tobacco extract, aerosol former, nicotine, and/or other active ingredient that can be used in a heat not burn device. For example, NEOSTIKS™ consumable aerosol source members for the GLO™ product by British American Tobacco and in the HEETS™ consumable aerosol source members for the IQOS™ product by Philip Morris International, Inc. In the case of either electronic cigarettes or heat-not-burn devices, the control body may be reusable, whereas the cartridge/aerosol source member may be configured for a limited number of uses and/or configured to be disposable. Various mechanisms may connect the cartridge/aerosol source member to the control body to result in a threaded engagement, a press-fit engagement, an interference fit, a sliding fit, a magnetic engagement, or the like.

The control body and cartridge/aerosol source member may include separate, respective housings or outer bodies, which may be formed of any of a number of different materials. The housing may be formed of any suitable, structurally-sound material. In some examples, the housing may be formed of a metal or alloy, such as stainless steel, aluminum or the like. Other suitable materials include various plastics (e.g., polycarbonate), metal-plating over plastic, ceramics and the like.

The cartridge (i.e. aerosol source member) may include the aerosol precursor composition. In order to produce aerosol from the aerosol precursor composition, the aerosol production component (e.g., heating element, piezoelectric/piezomagnetic mesh) may be positioned in contact with or proximate the aerosol precursor composition, such as across the control body and cartridge, or in the control body in which the aerosol source member may be positioned. The control body may include a power source, which may be rechargeable or replaceable, and thereby the control body may be reused with multiple cartridges/aerosol source members.

The control body may also include means to activate the aerosol delivery device such as a pushbutton, touch-sensitive surface or the like for manual control of the device. Additionally or alternatively, the control body may include a flow sensor to detect when a user draws on the cartridge/aerosol source member to thereby activate the aerosol delivery device. In some embodiments, the control body may include the heating element rather than being in the consumable or cartridge in other embodiments.

In various implementations, the aerosol delivery device according to the present disclosure may have a variety of overall shapes, including, but not limited to an overall shape that may be defined as being substantially rod-like or substantially tubular shaped or substantially cylindrically shaped. In the implementations shown in and described with reference to the accompanying figures, the aerosol delivery device has a substantially round cross-section; however, other cross-sectional shapes (e.g., oval, square, rectangle, triangle, etc.) also are encompassed by the present disclosure. Such language that is descriptive of the physical shape of the article may also be applied to the individual components thereof, including the control body and the cartridge/aerosol source member. In other implementations, the control body may take another handheld shape, such as a small box shape.

In more specific implementations, one or both of the control body and the cartridge/aerosol source member may be referred to as being disposable or as being reusable. For example, the control body may have a power source such as a replaceable battery or a rechargeable battery, SSB, thin-film SSB, capacitor, photovoltaic, rechargeable supercapacitor, lithium-ion or hybrid lithium-ion supercapacitor, or the like. One example of a power source is a TKI-1550 rechargeable lithium-ion battery produced by Tadiran Batteries GmbH of Germany. In another implementation, a useful power source may be a N50-AAA CADNICA nickel-cadmium cell produced by Sanyo Electric Company, Ltd., of Japan. In other implementations, a plurality of such batteries, for example providing 1.2-volts each, may be connected in series. In some implementations, the power source is configured to provide an output voltage. The power source can power the aerosol production component that is powerable to produce an aerosol from an aerosol precursor composition. The power source may be connected with any type of recharging technology, such as a charging accessory as further discussed below.

Examples of power sources are described in U.S. Pat. No. 9,484,155 to Peckerar et al.; and U.S. Pat. App. Pub. No. 2017/0112191 to Sur et al., filed Oct. 21, 2015, the disclosures of which are incorporated herein by reference. Other examples of a suitable power source are provided in U.S. Pat. App. Pub. No. 2014/0283855 to Hawes et al., U.S. Pat. App. Pub. No. 2014/0014125 to Fernando et al., U.S. Pat. App. Pub. No. 2013/0243410 to Nichols et al., U.S. Pat. App. Pub. No. 2010/0313901 to Fernando et al., and U.S. Pat. No. 9,439,454 to Fernando et al., all of which are incorporated herein by reference. With respect to the flow sensor, representative current regulating components and other current controlling components including various microcontrollers, sensors, and switches for aerosol delivery devices are described in U.S. Pat. No. 4,735,217 to Gerth et al.; U.S. Pat. Nos. 4,922,901, 4,947,874, and 4,947,875, all to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al.; U.S. Pat. No. 8,205,622 to Pan; U.S. Pat. No. 8,881,737 to Collet et al.; U.S. Pat. No. 9,423,152 to Ampolini et al.; U.S. Pat. No. 9,439,454 to Fernando et al.; and U.S. Pat. App. Pub. No. 2015/0257445 to Henry et al., all of which are incorporated herein by reference.

Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. 6,164,287 to White; U.S. Pat No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; PCT Pat. App. Pub. No. WO 2010/091593 to Hon; and PCT Pat. App. Pub. No. WO 2013/089551 to Foo, each of which is incorporated herein by reference. Further, U.S. Pat. App. Pub. No. 2017/0099877 to Worm et al., discloses capsules that may be included in aerosol delivery devices and fob-shape configurations for aerosol delivery devices, and is incorporated herein by reference. A variety of the materials disclosed by the foregoing documents may be incorporated into the present devices in various implementations, and all of the foregoing disclosures are incorporated herein by reference.

Yet other features, controls or components that can be incorporated into aerosol delivery devices of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. App. Pub. No. 2005/0016550 to Katase; U.S. Pat. No. 8,689,804 to Fernando et al.; U.S. Pat. App. Pub. No. 2013/0192623 to Tucker et al.; U.S. Pat. No. 9,427,022 to Leven et al.; U.S. Pat. App. Pub. No. 2013/0180553 to Kim et al.; U.S. Pat. App. Pub. No. 2014/0000638 to Sebastian et al.; U.S. Pat. App. Pub. No. 2014/0261495 to Novak et al.; and U.S. Pat. No. 9,220,302 to DePiano et al., all of which are incorporated herein by reference.

In another aspect, the present disclosure may be directed to kits that provide a variety of components as described herein. For example, a kit may comprise a control body with one or more cartridges or aerosol source members. A kit may further include a charging accessory described below, along with one or more batteries, and a control body with one or more cartridges. A kit may further comprise a plurality of cartridges and one or more batteries and/or a charging accessory. In the above embodiments, the cartridges or the control bodies may be provided with a heating member inclusive thereto. The inventive kits may further include a case (or other packaging, carrying, or storage component) that accommodates one or more of the further kit components. Alternatively, a charging accessory may be a case in one of the kits. The case could be a reusable hard or soft container. Further, the case could be simply a box or other packaging structure.

FIGS. 1 and 2 illustrate implementations of an aerosol delivery device including a control body and a cartridge in the case of an electronic cigarette. In this regard, FIGS. 1 and 2 illustrate an aerosol delivery device 100 according to an example implementation of the present disclosure. As indicated, the aerosol delivery device may include a control body 102 (i.e. battery portion) and a cartridge 104. As described below, operation of the device, such as when the cartridge 104 is installed, may require the authentication along with age verification. The control body and the cartridge can be permanently or detachably aligned in a functioning relationship. In this regard, FIG. 1 illustrates a perspective view of the aerosol delivery device in a coupled configuration, whereas FIG. 2 illustrates a partially cut-away side view of the aerosol delivery device in a decoupled configuration. The aerosol delivery device may, for example, be substantially rod-like, substantially tubular shaped, or substantially cylindrically shaped in some implementations when the control body and the cartridge are in an assembled configuration.

The control body 102 and the cartridge 104 can be configured to engage one another by a variety of connections, such as a press fit (or interference fit) connection, a threaded connection, a magnetic connection, or the like. As such, the control body may include a first engaging element (e.g., a coupler) that is adapted to engage a second engaging element (e.g., a connector) on the cartridge. The first engaging element and the second engaging element may be reversible. As an example, either of the first engaging element or the second engaging element may be a male thread, and the other may be a female thread. As a further example, either the first engaging element or the second engaging element may be a magnet, and the other may be a metal or a matching magnet. In particular implementations, engaging elements may be defined directly by existing components of the control body and the cartridge. For example, the housing of the control body may define a cavity at an end thereof that is configured to receive at least a portion of the cartridge (e.g., a storage tank or other shell-forming element of the cartridge). In particular, a storage tank of the cartridge may be at least partially received within the cavity of the control body while a mouthpiece of the cartridge remains exposed outside of the cavity of the control body. The cartridge may be retained within the cavity formed by the control body housing, such as by an interference fit (e.g., through use of detents and/or other features creating an interference engagement between an outer surface of the cartridge and an interior surface of a wall forming the control body cavity), by a magnetic engagement (e.g., though use of magnets and/or magnetic metals positioned within the cavity of the control body and positioned on the cartridge), or by other suitable techniques.

As seen in the cut-away view illustrated in FIG. 2, the control body 102 and cartridge 104 each include a number of respective components. The components illustrated in FIG. 2 are representative of the components that may be present in a control body and cartridge and are not intended to limit the scope of components that are encompassed by the present disclosure. In one embodiment, the control body 102 may be referred to as a battery portion. As shown, for example, the control body 102 can be formed of a housing 206 (sometimes referred to as a control body shell) that can include a control component 208 (e.g., processing circuitry, etc.), a flow sensor 210, a power source 212 (e.g., battery, supercapacitor), and an indicator 214 (e.g., LED, quantum dot-based LED), and such components can be variably aligned. The power source may be rechargeable, and the control component may include a switch and processing circuitry coupled to the flow sensor and the switch. The processing circuitry may be configured to prevent access (lock) the device depending on the authentication or age verification status. In one example, the device may start in a locked state in which usage is prevented, but will be usable once the device is authenticated upon receipt of the correct control signal at the device. In other words, the default state of the device may be locked and authentication (along with age verification) unlocks the device.

The cartridge 104 can be formed of a housing 216 (sometimes referred to as the cartridge shell) enclosing a reservoir 218 configured to retain the aerosol precursor composition, and including a heating element 220 (aerosol production component). In various configurations, this structure may be referred to as a tank; and accordingly, the terms "cartridge," "tank" and the like may be used interchangeably to refer to a shell or other housing enclosing a reservoir for aerosol precursor composition, and including a heating element.

As shown, in some examples, the reservoir 218 may be in fluid communication with a liquid transport element 222 adapted to wick or otherwise transport an aerosol precursor composition stored in the reservoir housing to the heating element 220. In some examples, a valve may be positioned between the reservoir and heating element, and configured to control an amount of aerosol precursor composition passed or delivered from the reservoir to the heating element.

Various examples of materials configured to produce heat when electrical current is applied therethrough may be employed to form the heating element 220. The heating element in these examples may be a resistive heating element such as a wire coil, micro heater or the like. Example materials from which the heating element may be formed include Kanthal (FeCrAl), nichrome, nickel, stainless steel, indium tin oxide, tungsten, molybdenum disilicide (MoSi2), molybdenum silicide (MoSi), molybdenum disilicide doped with aluminum (Mo(Si,Al)2), titanium, platinum, silver, palladium, alloys of silver and palladium, graphite and graphite-based materials (e.g., carbon-based foams and yarns), conductive inks, boron doped silica, and ceramics (e.g., positive or negative temperature coefficient ceramics). The heating element may be resistive heating element or a heating element configured to generate heat through induction. The heating element may be coated by heat conductive ceramics such as aluminum nitride, silicon carbide, beryllium oxide, alumina, silicon nitride, or their composites. Example implementations of heating elements useful in aerosol delivery devices according to the present disclosure are further described below, and can be incorporated into devices such as those described herein.

An opening 224 may be present in the housing 216 (e.g., at the mouth end) to allow for egress of formed aerosol from the cartridge 104.

The cartridge 104 also may include one or more electronic components 226, which may include an integrated circuit, a memory component (e.g., EEPROM, flash memory), a sensor, or the like. The electronic components may be adapted to communicate with the control component 208 and/or with an external device by wired or wireless means. The electronic components may be positioned anywhere within the cartridge or a base 228 thereof.

Although the control component 208 and the flow sensor 210 are illustrated separately, it is understood that various electronic components including the control component and the flow sensor may be combined on a circuit board (e.g., PCB) that supports and electrically connects the electronic components. Further, the circuit board may be positioned horizontally relative to the illustration of FIG. 1 in that the circuit board can be lengthwise parallel to the central axis of the control body. In some examples, the air flow sensor may comprise its own circuit board or other base element to which it can be attached. In some examples, a flexible circuit board may be utilized. A flexible circuit board may be configured into a variety of shapes, include substantially tubular shapes. In some examples, a flexible circuit board may be combined with, layered onto, or form part or all of a heater substrate.

The control body 102 and the cartridge 104 may include components adapted to facilitate a fluid engagement therebetween. As illustrated in FIG. 2, the control body can include a coupler 230 having a cavity 232 therein. The base 228 of the cartridge can be adapted to engage the coupler and can include a projection 234 adapted to fit within the cavity. Such engagement can facilitate a stable connection between the control body and the cartridge as well as establish an electrical connection between the power source 212 and control component 208 in the control body and the heating element 220 in the cartridge. Further, the housing 206 can include an air intake 236, which may be a notch in the housing where it connects to the coupler that allows for passage of ambient air around the coupler and into the housing where it then passes through the cavity 232 of the coupler and into the cartridge through the projection 234.

A coupler and a base useful according to the present disclosure are described in U.S. Pat. App. Pub. No. 2014/0261495 to Novak et al., which is incorporated herein by reference. For example, the coupler 230 as seen in FIG. 2 may define an outer periphery 238 configured to mate with an inner periphery 240 of the base 228. In one example the inner periphery of the base may define a radius that is substantially equal to, or slightly greater than, a radius of the outer periphery of the coupler. Further, the coupler may define one or more protrusions 242 at the outer periphery configured to engage one or more recesses 244 defined at the inner periphery of the base. However, various other examples of structures, shapes and components may be employed to couple the base to the coupler. In some examples the connection between the base of the cartridge 104 and the coupler of the control body 102 may be substantially permanent, whereas in other examples the connection therebetween may be releasable such that, for example, the control body may be reused with one or more additional cartridges that may be disposable and/or refillable.

The reservoir 218 illustrated in FIG. 2 can be a container or can be a fibrous reservoir, as presently described. For example, the reservoir can comprise one or more layers of nonwoven fibers substantially formed into the shape of a tube encircling the interior of the housing 216, in this example. An aerosol precursor composition can be retained in the reservoir. Liquid components, for example, can be sorptively retained by the reservoir. The reservoir can be in fluid connection with the liquid transport element 222. The liquid transport element can transport the aerosol precursor composition stored in the reservoir via capillary action—or via a micro pump— to the heating element 220 that is in the form of a metal wire coil in this example. As such, the heating element is in a heating arrangement with the liquid transport element.

In some examples, a microfluidic chip may be embedded in the reservoir 218, and the amount and/or mass of aerosol precursor composition delivered from the reservoir may be controlled by a micro pump, such as one based on microelectromechanical systems (MEMS) technology. Other example implementations of reservoirs and transport elements useful in aerosol delivery devices according to the present disclosure are further described herein, and such reservoirs and/or transport elements can be incorporated into devices such as those described herein. In particular, specific combinations of heating members and transport elements as further described herein may be incorporated into devices such as those described herein.

In use, when a user draws on the aerosol delivery device 100, airflow is detected by the flow sensor 210, and the heating element 220 is activated to vaporize components of the aerosol precursor composition. Drawing upon the mouth end of the aerosol delivery device causes ambient air to enter the air intake 236 and pass through the cavity 232 in the coupler 230 and the central opening in the projection 234 of the base 228. In the cartridge 104, the drawn air combines with the formed vapor to form an aerosol. The aerosol is whisked, aspirated or otherwise drawn away from the heating element and out the opening 224 in the mouth end of the aerosol delivery device.

For further detail regarding implementations of an aerosol delivery device including a control body and a cartridge in the case of an electronic cigarette, see the above-cited U.S. patent application Ser. No. 15/836,086 to Sur; and U.S. patent application Ser. No. 15/916,834 to Sur et al.; as well as U.S. patent application Ser. No. 15/916,696 to Sur, filed Mar. 9, 2018, which is also incorporated herein by reference.

FIGS. 3-6 illustrate implementations of an aerosol delivery device including a control body and an aerosol source member in the case of a heat-not-burn device. More specifically, FIG. 3 illustrates an aerosol delivery device 300 according to an example implementation of the present disclosure. The aerosol delivery device may include a control body 302 and an aerosol source member 304. In various implementations, the aerosol source member and the control body can be permanently or detachably aligned in a functioning relationship. In this regard, FIG. 3 illustrates the aerosol delivery device in a coupled configuration, whereas FIG. 4 illustrates the aerosol delivery device in a decoupled configuration.

As shown in FIG. 4, in various implementations of the present disclosure, the aerosol source member 304 may comprise a heated end 406, which is configured to be inserted into the control body 302, and a mouth end 408, upon which a user draws to create the aerosol. In various implementations, at least a portion of the heated end may include an aerosol precursor composition 410.

In various implementations, the aerosol source member 304, or a portion thereof, may be wrapped in an exterior overwrap material 412, which may be formed of any material useful for providing additional structure and/or support for the aerosol source member. In various implementations, the exterior overwrap material may comprise a material that resists transfer of heat, which may include a paper or other fibrous material, such as a cellulose material. The exterior overwrap material may also include at least one filler material imbedded or dispersed within the fibrous material. In various implementations, the filler material may have the form of water insoluble particles. Additionally, the filler material may incorporate inorganic components. In various implementations, the exterior overwrap may be formed of multiple layers, such as an underlying, bulk layer and an overlying layer, such as a typical wrapping paper in a cigarette. Such materials may include, for example, lightweight "rag fibers" such as flax, hemp, sisal, rice straw, and/or esparto. The exterior overwrap may also include a material typically used in a filter element of a conventional cigarette, such as cellulose acetate.

Further, an excess length of the overwrap at the mouth end 408 of the aerosol source member may function to simply separate the aerosol precursor composition 410 from the mouth of a consumer or to provide space for positioning of a filter material, as described below, or to affect draw on the article or to affect flow characteristics of the vapor or aerosol leaving the device during draw. Further discussion relating to the configurations for overwrap materials that may be used with the present disclosure may be found in the above-cited U.S. Pat. No. 9,078,473 to Worm et al.

In various implementations other components may exist between the aerosol precursor composition 410 and the mouth end 408 of the aerosol source member 304, wherein the mouth end may include a filter 414, which may, for example, be made of a cellulose acetate or polypropylene material. The filter may additionally or alternatively contain strands of tobacco containing material, such as described in U.S. Pat. No. 5,025,814 to Raker et al., which is incorporated herein by reference in its entirety. In various implementations, the filter may increase the structural integrity of the mouth end of the aerosol source member, and/or provide filtering capacity, if desired, and/or provide resistance to draw. In some implementations one or any combination of the following may be positioned between the aerosol precursor composition and the mouth end: an air gap; phase change materials for cooling air; flavor releasing media; ion exchange fibers capable of selective chemical adsorption; aerogel particles as filter medium; and other suitable materials.

Various implementations of the present disclosure employ one or more conductive heating elements to heat the aerosol precursor composition 410 of the aerosol source member 304. In various implementations, the heating element may be provided in a variety forms, such as in the form of a foil, a foam, a mesh, a hollow ball, a half ball, discs, spirals, fibers, wires, films, yarns, strips, ribbons, or cylinders. Such heating elements often comprise a metal material and are configured to produce heat as a result of the electrical resistance associated with passing an electrical current therethrough. Such resistive heating elements may be positioned in direct contact with, or in proximity to, the aerosol source member and particularly, the aerosol precursor composition of the aerosol source member. The heating element may be located in the control body and/or the aerosol source member. In various implementations, the aerosol precursor composition may include components (i.e., heat conducting constituents) that are imbedded in, or otherwise part of, the substrate portion that may serve as, or facilitate the function of, the heating assembly. Some examples of various heating members and elements are described in U.S. Pat. No. 9,078,473 to Worm et al.

Some non-limiting examples of various heating element configurations include configurations in which a heating element is placed in proximity with the aerosol source member 304. For instance, in some examples, at least a portion of a heating element may surround at least a portion of an aerosol source member. In other examples, one or more heating elements may be positioned adjacent an exterior of an aerosol source member when inserted in the control body 302. In other examples, at least a portion of a heating element may penetrate at least a portion of an aerosol source member (such as, for example, one or more prongs and/or spikes that penetrate an aerosol source member), when the aerosol source member is inserted into the control body. In some instances, the aerosol precursor composition may include a structure in contact with, or a plurality of beads or particles imbedded in, or otherwise part of, the aerosol precursor composition that may serve as, or facilitate the function of the heating element.

FIG. 5 illustrates a front view of an aerosol delivery device 300 according to an example implementation of the present disclosure, and FIG. 6 illustrates a sectional view through the aerosol delivery device of FIG. 5. In particular, the control body 302 of the depicted implementation may comprise a housing 516 that includes an opening 518 defined in an engaging end thereof, a flow sensor 520 (e.g., a puff sensor or pressure switch), a control component 522 (e.g., processing circuitry, etc.), a power source 524 (e.g., battery, supercapacitor), and an end cap that includes an indicator 526 (e.g., a LED). The power source may be rechargeable, and the control component may include a switch and processing circuitry coupled to the flow sensor and the switch. The processing circuitry may be configured to prevent operation with the switch if the age verification fails as further discussed below. The default state of the device may be with the switch not connected and the switch is connected upon authentication (which may be based on verification).

In one implementation, the indicator 526 may comprise one or more LEDs, quantum dot-based LEDs or the like. The indicator can be in communication with the control component 522 and be illuminated, for example, when a user draws on the aerosol source member 304, when coupled to the control body 302, as detected by the flow sensor 520.

The control body 302 of the depicted implementation includes one or more heating assemblies 528 (individually or collectively referred to a heating assembly) configured to heat the aerosol precursor composition 410 of the aerosol source member 304. Although the heating assembly of various implementations of the present disclosure may take a variety of forms, in the particular implementation depicted in FIGS. 5 and 6, the heating assembly comprises an outer cylinder 530 and a heating element 532 (aerosol production component), which in this implementation comprises a plurality of heater prongs that extend from a receiving base 534 (in various configurations, the heating assembly or more specifically the heater prongs may be referred to as a heater). In the depicted implementation, the outer cylinder comprises a double-walled vacuum tube constructed of stainless steel to maintain heat generated by the heater prongs within the outer cylinder, and more particularly, maintain heat generated by heater prongs within the aerosol precursor composition. In various implementations, the heater prongs may be constructed of one or more conductive materials, including, but not limited to, copper, aluminum, platinum, gold, silver, iron, steel, brass, bronze, graphite, or any combination thereof.

As illustrated, the heating assembly 528 may extend proximate an engagement end of the housing 516, and may be configured to substantially surround a portion of the heated end 406 of the aerosol source member 304 that includes the aerosol precursor composition 410. In such a manner, the heating assembly may define a generally tubular configuration. As illustrated in FIGS. 5 and 6, the heating element 532 (e.g., plurality of heater prongs) is surrounded by the outer cylinder 530 to create a receiving chamber 536. In such a manner, in various implementations the outer cylinder may comprise a nonconductive insulating material and/or construction including, but not limited to, an insulating polymer (e.g., plastic or cellulose), glass, rubber, ceramic, porcelain, a double-walled vacuum structure, or any combinations thereof.

In some implementations, one or more portions or components of the heating assembly 528 may be combined with, packaged with, and/or integral with (e.g., embedded within) the aerosol precursor composition 410. For example, in some implementations the aerosol precursor composition may be formed of a material as described above and may include one or more conductive materials mixed therein. In some of these implementations, contacts may be connected directly to the aerosol precursor composition such that, when the aerosol source member is inserted into the receiving chamber of the control body, the contacts make electrical connection with the electrical energy source. Alternatively, the contacts may be integral with the electrical energy source and may extend into the receiving chamber such that, when the aerosol source member is inserted into the receiving chamber of the control body, the contacts make electrical connection with the aerosol precursor composition. Because of the presence of the conductive material in the aerosol precursor composition, the application of power from the electrical energy source to the aerosol precursor composition allows electrical current to flow and thus produce heat from the conductive material. Thus, in some implementations the heating element may be described as being integral with the aerosol precursor composition. As a non-limiting example, graphite or other suitable, conductive material may be mixed with, embedded in, or otherwise present directly on or within the material forming the aerosol precursor composition to make the heating element integral with the medium.

As noted above, in the illustrated implementation, the outer cylinder 530 may also serve to facilitate proper positioning of the aerosol source member 304 when the aerosol source member is inserted into the housing 516. In various implementations, the outer cylinder of the heating assembly 528 may engage an internal surface of the housing to provide for alignment of the heating assembly with respect to the housing. Thereby, as a result of the fixed coupling between the heating assembly, a longitudinal axis of the heating assembly may extend substantially parallel to a longitudinal axis of the housing. In particular, the support cylinder may extend from the opening 518 of the housing to the receiving base 534 to create the receiving chamber 536.

The heated end 406 of the aerosol source member 304 is sized and shaped for insertion into the control body 302. In various implementations, the receiving chamber 536 of the control body may be characterized as being defined by a wall with an inner surface and an outer surface, the inner surface defining the interior volume of the receiving chamber. For example, in the depicted implementations, the outer cylinder 530 defines an inner surface defining the interior volume of the receiving chamber. In the illustrated implementation, an inner diameter of the outer cylinder may be slightly larger than or approximately equal to an outer diameter of a corresponding aerosol source member (e.g., to create a sliding fit) such that the outer cylinder is configured to guide the aerosol source member into the proper position (e.g., lateral position) with respect to the control body. Thus, the largest outer diameter (or other dimension depending upon the specific cross-sectional shape of the implementations) of the aerosol source member may be sized to be less than the inner diameter (or other dimension) at the inner surface of the wall of the open end of the receiving chamber in the control body. In some implementations, the difference in the respective diameters may be sufficiently small so that the aerosol source member fits snugly into the receiving chamber, and frictional forces prevent the aerosol source member from being moved without an applied force. On the other hand, the difference may be sufficient to allow the aerosol source member to slide into or out of the receiving chamber without requiring undue force.

In the illustrated implementation, the control body 302 is configured such that when the aerosol source member 304 is inserted into the control body, the heating element 532 (e.g., heater prongs) is located in the approximate radial center of at least a portion of the aerosol precursor composition 410 of the heated end 406 of the aerosol source member. In such a manner, when used in conjunction with a solid or semi-solid aerosol precursor composition, the heater prongs may be in direct contact with the aerosol precursor composition. In other implementations, such as when used in conjunction with an extruded aerosol precursor composition that defines a tube structure, the heater prongs may be located inside of a cavity defined by an inner surface of the extruded tube structure, and would not contact the inner surface of the extruded tube structure.

During use, the consumer initiates heating of the heating assembly 528, and in particular, the heating element 532 that is adjacent the aerosol precursor composition 410 (or a specific layer thereof). Heating of the aerosol precursor composition releases the inhalable substance within the aerosol source member 304 so as to yield the inhalable substance. When the consumer inhales on the mouth end 408 of the aerosol source member, air is drawn into the aerosol source member through an air intake 538 such as openings or apertures in the control body 302. The combination of the drawn air and the released inhalable substance is inhaled by the consumer as the drawn materials exit the mouth end of the aerosol source member. In some implementations, to initiate heating, the consumer may manually actuate a push-button or similar component that causes the heating element of the heating assembly to receive electrical energy from the battery or other energy source. The electrical energy may be supplied for a pre-determined length of time or may be manually controlled.

In some implementations, flow of electrical energy does not substantially proceed in between puffs on the device 300 (although energy flow may proceed to maintain a baseline temperature greater than ambient temperature—e.g., a temperature that facilitates rapid heating to the active heating temperature). In the depicted implementation, however, heating is initiated by the puffing action of the consumer through use of one or more sensors, such as flow sensor 520. Once the puff is discontinued, heating will stop or be reduced. When the consumer has taken a sufficient number of puffs so as to have released a sufficient amount of the inhalable substance (e.g., an amount sufficient to equate to a typical smoking experience), the aerosol source member 304 may be removed from the control body 302 and discarded. In some implementations, further sensing elements, such as capacitive sensing elements and other sensors, may be used as discussed in U.S. patent application Ser. No. 15/707,461 to Phillips et al., which is incorporated herein by reference.

In various implementations, the aerosol source member 304 may be formed of any material suitable for forming and maintaining an appropriate conformation, such as a tubular shape, and for retaining therein the aerosol precursor composition 410. In some implementations, the aerosol source member may be formed of a single wall or, in other implementations, multiple walls, and may be formed of a material (natural or synthetic) that is heat resistant so as to retain its structural integrity—e.g., does not degrade—at least at a temperature that is the heating temperature provided by the electrical heating element, as further discussed herein. While in some implementations, a heat resistant polymer may be used, in other implementations, the aerosol source member may be formed from paper, such as a paper that is substantially straw-shaped. As further discussed herein, the aerosol source member may have one or more layers associated therewith that function to substantially prevent movement of vapor therethrough. In one example implementation, an aluminum foil layer may be laminated to one surface of the aerosol source member. Ceramic materials also may be used. In further implementations, an insulating material may be used so as not to unnecessarily move heat away from the aerosol precursor composition. Further example types of components and materials that may be used to provide the functions described above or be used as alternatives to the materials and components noted above can be those of the types set forth in U.S. Pat. App. Pub. Nos. 2010/00186757 to Crooks et al., 2010/00186757 to Crooks et al., and 2011/0041861 to Sebastian et al., all of which are incorporated herein by reference.

In the depicted implementation, the control body 302 includes a control component 522 that controls the various functions of the aerosol delivery device 300, including providing power to the electrical heating element 532. For example, the control component may include processing circuitry (which may be connected to further components, as further described herein) that is connected by electrically conductive wires (not shown) to the power source 524. In various implementations, the processing circuitry may control when and how the heating assembly 528, and particularly the heater prongs, receives electrical energy to heat the aerosol precursor composition 410 for release of the inhalable substance for inhalation by a consumer. In some implementations, such control may be activated by a flow sensor 520 as described in greater detail above.

As seen in FIGS. 5 and 6, the heating assembly 528 of the depicted implementation comprises an outer cylinder 530 and a heating element 532 (e.g., plurality of heater prongs) that extend from a receiving base 534. In some implementations, such as those wherein the aerosol precursor composition 410 comprises a tube structure, the heater prongs may be configured to extend into a cavity defined by the inner surface of the aerosol precursor composition. In other implementations, such as the depicted implementation wherein the aerosol precursor composition comprises a solid or semi-solid, the plurality of heater prongs are configured to penetrate into the aerosol precursor composition contained in the heated end 406 of the aerosol source member 304 when the aerosol source member is inserted into the control body 302. In such implementations, one or more of the components of the heating assembly, including the heater prongs and/or the receiving base, may be constructed of a non-stick or stick- resistant material, for example, certain aluminum, copper, stainless steel, carbon steel, and ceramic materials. In other implementations, one or more of the components of the heating assembly, including the heater prongs and/or the receiving base, may include a non-stick coating, including, for example, a polytetrafluoroethylene (PTFE) coating, such as Teflon®, or other coatings, such as a stick-resistant enamel coating, or a ceramic coating, such as Greblon®, or Thermolon™, or a ceramic coating, such as Greblon®, or Thermolon™.

In addition, although in the depicted implementation there are multiple heater prongs 532 that are substantially equally distributed about the receiving base 534, it should be noted that in other implementations, any number of heater prongs may be used, including as few as one, with any other suitable spatial configuration. Furthermore, in various implementations the length of the heater prongs may vary. For example, in some implementations the heater prongs may comprise small projections, while in other implementations the heater prongs may extend any portion of the length of the receiving chamber 536, including up to about 25%, up to about 50%, up to about 75%, and up to about the full length of the receiving chamber. In still other implementations, the heating assembly 528 may take on other configurations. Examples of other heater configurations that may be adapted for use in the present invention per the discussion provided above can be found in U.S. Pat. No. 5,060,671 to Counts et al., U.S. Pat. No. 5,093,894 to Deevi et al., U.S. Pat. No. 5,224,498 to Deevi et al., U.S. Pat. No. 5,228,460 to Sprinkel Jr., et al., U.S. Pat. No. ,322,075 to Deevi et al., U.S. Pat. No. 5,353,813 to Deevi et al., U.S. Pat. No. 5,468,936 to Deevi et al., U.S. Pat. No. 5,498,850 to Das, U.S. Pat. No. 5,659,656 to Das, U.S. Pat. No. 5,498,855 to Deevi et al., U.S. Pat. No. 5,530,225 to Hajaligol, U.S. Pat. No. 5,665,262 to Hajaligol, and U.S. Pat. No. 5,573,692 to Das et al.; and U.S. Pat. No. 5,591,368 to Fleischhauer et al., which are incorporated herein by reference.

In various implementations, the control body 302 may include an air intake 538 (e.g., one or more openings or apertures) therein for allowing entrance of ambient air into the interior of the receiving chamber 536. In such a manner, in some implementations the receiving base 534 may also include an air intake. Thus, in some implementations when a consumer draws on the mouth end of the aerosol source member 304, air can be drawn through the air intake of the control body and the receiving base into the receiving chamber, pass into the aerosol source member, and be drawn through the aerosol precursor composition 410 of the aerosol source member for inhalation by the consumer. In some implementations, the drawn air carries the inhalable substance through the optional filter 414 and out of an opening at the mouth end 408 of the aerosol source member. With the heating element 532 positioned inside the aerosol precursor composition, the heater prongs may be activated to heat the aerosol precursor composition and cause release of the inhalable substance through the aerosol source member.

As described above with reference to FIGS. 5 and 6 in particular, various implementations of the present disclosure employ a conductive heater to heat the aerosol precursor composition 410. As also indicated above, various other implementations employ an induction heater to heat the aerosol precursor composition. In some of these implementations, the heating assembly 528 may be configured as an induction heater that comprises a transformer with an induction transmitter and an induction receiver. In implementations in which the heating assembly is configured as the induction heater, the outer cylinder 530 may be configured as the induction transmitter, and the heating element 532 (e.g., plurality of heater prongs) that extend from the receiving base 534 may be configured as the induction receiver. In various implementations, one or both of the induction transmitter and induction receiver may be located in the control body 302 and/or the aerosol source member 304.

In various implementations, the outer cylinder 530 and heating element 532 as the induction transmitter and induction receiver may be constructed of one or more conductive materials, and in further implementations the induction receiver may be constructed of a ferromagnetic material including, but not limited to, cobalt, iron, nickel, and combinations thereof. In one example implementation, the foil material is constructed of a conductive material and the heater prongs are constructed of a ferromagnetic material. In various implementations, the receiving base may be constructed of a non-conductive and/or insulating material.

The outer cylinder 530 as the induction transmitter may include a laminate with a foil material that surrounds a support cylinder. In some implementations, the foil material may include an electrical trace printed thereon, such as, for example, one or more electrical traces that may, in some implementations, form a helical coil pattern when the foil material is positioned around the heating element 532 as the induction receiver. The foil material and support cylinder may each define a tubular configuration. The support cylinder may be configured to support the foil material such that the foil material does not move into contact with, and thereby short-circuit with, the heater prongs. In such a manner, the support cylinder may comprise a nonconductive material, which may be substantially transparent to an oscillating magnetic field produced by the foil material. In various implementations, the foil material may be imbedded in, or otherwise coupled to, the support cylinder. In the illustrated implementation, the foil material is engaged with an outer surface of the support cylinder; however, in other implementations, the foil material may be positioned at an inner surface of the support cylinder or be fully imbedded in the support cylinder.

The foil material of the outer cylinder 530 may be configured to create an oscillating magnetic field (e.g., a magnetic field that varies periodically with time) when alternating current is directed through it. The heater prongs of the heating element 532 may be at least partially located or received within the outer cylinder and include a conductive material. By directing alternating current through the foil material, eddy currents may be generated in the heater prongs via induction. The eddy currents flowing through the resistance of the material defining the heater prongs may heat it by Joule heating (i.e., through the Joule effect). The heater prongs may be wirelessly heated to form an aerosol from the aerosol precursor composition 410 positioned in proximity to the heater prongs.

Other implementations of the aerosol delivery device, control body and aerosol source member are described in the above-cited U.S. patent application Ser. No. 15/916,834 to Sur et al.; U.S. patent application Ser. No. 15/916,696 to Sur; and U.S. patent application Ser. No. 15/836,086 to Sur.

FIGS. 7 and 8 illustrate implementations of an aerosol delivery device including a control body and a cartridge in the case of a no-heat-no-burn device. In this regard, FIG. 7 illustrates a side view of an aerosol delivery device 700 including a control body 702 and a cartridge 704, according to various example implementations of the present disclosure. In particular, FIG. 7 illustrates the control body and the cartridge coupled to one another. The control body and the cartridge may be detachably aligned in a functioning relationship.

FIG. 8 more particularly illustrates the aerosol delivery device 700, in accordance with some example implementations. As seen in the cut-away view illustrated therein, again, the aerosol delivery device can comprise a control body 702 and a cartridge 704 each of which include a number of respective components. The components illustrated in FIG. 8 are representative of the components that may be present in a control body and cartridge and are not intended to limit the scope of components that are encompassed by the present disclosure. As shown, for example, the control body can be formed of a control body housing or shell 806 that can include a control component 808 (e.g., processing circuitry, etc.), an input device 810, a power source 812 and an indicator 814 (e.g., LED, quantum dot-based LED), and such components can be variably aligned. Here, a particular example of a suitable control component includes the PIC16 (L)F1713/6 microcontrollers from Microchip Technology Inc., which is described in Microchip Technology, Inc., AN2265, Vibrating Mesh Nebulizer Reference Design (2016), which is incorporated by reference.

The cartridge 704 can be formed of a housing—referred to at times as a cartridge shell 816—enclosing a reservoir 818 configured to retain the aerosol precursor composition, and including a nozzle 820 having a piezoelectric/piezomagnetic mesh (aerosol production component). Similar to above, in various configurations, this structure may be referred to as a tank.

The reservoir 818 illustrated in FIG. 8 can be a container or can be a fibrous reservoir, as presently described. The reservoir may be in fluid communication with the nozzle 820 for transport of an aerosol precursor composition stored in the reservoir housing to the nozzle. An opening 822 may be present in the cartridge shell 816 (e.g., at the mouthend) to allow for egress of formed aerosol from the cartridge 704.

In some examples, a transport element may be positioned between the reservoir 818 and nozzle 820, and configured to control an amount of aerosol precursor composition passed or delivered from the reservoir to the nozzle. In some examples, a microfluidic chip may be embedded in the cartridge 704, and the amount and/or mass of aerosol precursor composition delivered from the reservoir may be controlled by one or more microfluidic components. One example of a microfluidic component is a micro pump 824, such as one based on mi croel ectrom echani c al systems (MEMS) technology. Examples of suitable micro pumps include the model MDP2205 micro pump and others from thinXXS Microtechnology AG, the mp5 and mp6 model micro pumps and others from Bartels Mikrotechnik GmbH, and piezoelectric micro pumps from T akas ago Fluidic Systems.

As also shown, in some examples, a micro filter 826 may be positioned between the micro pump 824 and nozzle 820 to filter aerosol precursor composition delivered to the nozzle. Like the micro pump, the micro filter is a microfluidic component. Examples of suitable micro filters include flow-through micro filters those manufactured using lab-on-a-chip (LOC) techniques.

In use, when the input device 810 detects user input to activate the aerosol delivery device, the piezoelectric/piezomagnetic mesh is activated to vibrate and thereby draw aerosol precursor composition through the mesh. This forms droplets of aerosol precursor composition that combine with air to form an aerosol. The aerosol is whisked, aspirated or otherwise drawn away from the mesh and out the opening 822 in the mouthend of the aerosol delivery device.

The aerosol delivery device 700 can incorporate the input device 810 such as a switch, sensor or detector for control of supply of electric power to the piezoelectric/piezomagnetic mesh of the nozzle 820 when aerosol generation is desired (e.g., upon draw during use). As such, for example, there is provided a manner or method of turning off power to the mesh when the aerosol delivery device is not being drawn upon during use, and for turning on power to actuate or trigger the production and dispensing of aerosol from the nozzle during draw. Additional representative types of sensing or detection mechanisms, structure and configuration thereof, components thereof, and general methods of operation thereof, are described above and in U.S. Pat. No. 5,261,424 to Sprinkel, Jr., U.S. Pat. No. 5,372,148 to McCafferty et al., and PCT Pat. App. Pub. No. WO 2010/003480 to Flick, all of which are incorporated herein by reference.

For more information regarding the above and other implementations of an aerosol delivery device in the case of a no-heat-no-burn device, see U.S. patent application Ser. No. to Sur., filed Jul. 17, 2017, which is incorporated herein by reference.

As described above, the aerosol delivery device of example implementations may include various electronic components in the context of an electronic cigarette, heat-not-burn device or no-heat-no-burn device, or even in the case of a device that includes the functionality of one or more of an electronic cigarette, heat-not-burn device or no-heat-no-burn device. FIG. 9 illustrates a circuit diagram of an aerosol delivery device 900 that may be or incorporate functionality of any one or more of aerosol delivery devices 100, 300, 700 according to various example implementations of the present disclosure.

As shown in FIG. 9, the aerosol delivery device 900 includes a control body 902 with a power source 904 and a control component 906 that may correspond to or include functionality of respective ones of the control body 102, 302, 702, power source 212, 524, 812, and control component 208, 522, 808. The aerosol delivery device also includes an aerosol production component 916 that may correspond to or include functionality of heating element 220, 532, or piezoelectric/piezomagnetic mesh of nozzle 820. The control body 902 may include the aerosol production component 916 or terminals 918 configured to connect the aerosol production component to the control body.

In some implementations, the control body 902 includes a sensor 908 configured to produce measurements of air flow. The sensor 908 may correspond to or include functionality of the flow sensor 210, 520 or input device 810. In these implementations, the control component 906 includes a switch 910 coupled to and between the power source 904 and the aerosol production component 916. The control component also includes processing circuitry 912 coupled to the sensor and the switch. The switch can be a Metal Oxide Semiconductor Field Effect Transistor (MOSFET) switch. The sensor may be connected to inter-integrated circuit (I2C), Vcc and/or ground of the processing circuitry.

The sensor 908 may further include the audio detector 1402 or the optical detector 1502 as shown and described with respect to FIGS. 11-15. The sensor 908 may detect a control signal that is used for authentication. Upon authentication, the switch 910 may be triggered to allow operation of the device. In some implementations, the processing circuitry 912 is configured to process the control signal and determine if it matches the correct signal saved in the memory chip. In other embodiments, the processing circuitry 912 may be configured to authenticate and/or verify the age of a user, and to output a signal (as indicated by arrow 922) to cause the switch 910 to switchably connect and disconnect an output voltage from the power source 904 to the aerosol production component 916 to power the aerosol production component for an aerosol-production time period or based on usage (e.g. cartridge insertion, device charging, etc.). In some implementations, the processing circuitry 912 is configured to output a pulse width modulation (PWM) signal. A duty cycle of the PWM signal is adjustable to cause the switch to switchably connect and disconnect the output voltage to the aerosol production component. The processing circuitry 912 may include the signal detector circuitry 1202 described with respect to FIG. 12.

In some implementations, the control component 906 further includes signal conditioning circuitry 914 coupled to the sensor 908 and the processing circuitry 912. The signal conditioning circuitry of such implementations may be configured to manipulate the operation of the switch 910. The signal conditioning circuitry will be described in greater detail below with reference to FIG. 10.

Although not shown, the processing circuitry 912 and/or the signal conditioning circuitry 914 may be coupled with or receive a control signal that is used for authentication or verification. The control signal may be received by the sensor 908. If the control signal is received and correct, then the processing circuitry 912 may turn on the switch 910 to allow operation of the aerosol delivery device. Alternatively or in addition, if the verification signal is not received or not correct, then the processing circuitry 912 may shut off the switch 910 to prevent operation of the aerosol delivery device 900. The switch 910 may be controlled by the processing circuitry 912, including being based on control signal detection by the sensor 908. The control signal at the sensor 908 may be analyzed by the processing circuitry 912. The age verification and authentication process may be used to determine when the connection is made. If the user is not verified or authenticated, the switch may be disconnected to prevent voltage being provided to the aerosol production component. Alternatively, if the switch is in a disconnected state, then if the user is not verified or authenticated, the switch will remain in a disconnected state. Likewise, when the user is verified or authenticated, the switch can establish a connection so that current will be able flow for usage of the device. In other words, when the user is verified or authenticated, the output voltage is permitted to be provided to the aerosol production component.

FIG. 10 illustrates a circuit diagram of signal conditioning circuitry 1000 that may correspond to signal conditioning circuitry 914, according to an example implementation of the present disclosure. As shown, in some implementations, the signal conditioning circuitry 1000 includes a signal conditioning chip 1001, and a bidirectional voltage-level translator 1002. One example of a suitable signal conditioning chip is the model ZAP 3456 from Zap-Tech corporation. And one example of a suitable bidirectional voltage-level translator is the model NVT 2003 bidirectional voltage-level translator from NXP Semiconductors.

In one example, as shown in FIG. 10, the signal conditioning chip 1001 can be connected to the bidirectional voltage-level translator 1002, and the bidirectional voltage-level translator can be connected to the 5V input and ground of the processing circuitry 912. Note that the values (e.g., voltage, resistances and capacitance) shown in FIG. 10 are for purposes of illustrating the example only, and unless stated otherwise, the values should not be taken as limiting in the present disclosure.

FIG. 11 illustrates an example system diagram for functional control of a device. FIG. 11 illustrates how a device 1106 communicates with an age verification system 1102 through a network 1103 and a host device 1104, in order to verify the user's age, which may also be used to authenticate the device 1106 periodically. The age verification system 1102 is coupled with the host device 1104 over a network 1103. Although not shown, the age verification system 1102 may be coupled with the device 1106 over the network 1103.

The device 1106 may be any aerosol delivery device, including for example an electronic nicotine delivery systems ("ENDS") device according to various embodiments described above. In one embodiment, the device 1106 may be or may include a charging accessory such as the accessory described in U.S. patent application Ser. No. 16/415,460, entitled "AUTHENTICATION AND AGE VERIFICATION FOR AN AEROSOL DELIVERY DEVICE," which claims priority to U.S. Provisional App. No. 62/282,222 on Apr. 2, 2019, the entire disclosures of each of which are hereby incorporated by reference. Other example chargers or charging accessories that may be used in combination with various embodiments are further described in U.S. Pat. Pub. No. 2019/0089180 to Raj esh Sur; U.S. Pat. Pub. No. 2015/0224268 to Henry et al.; U.S. Pat. No. 10,206,431 to Sur et al.; each of which is hereby incorporated by reference.

As described, the age verification system 1102 may not only verify an age (e.g. for an age restricted product), but may also provide authentication or user identification (e.g. for an actual purchase or to prevent theft). The authentication and age verification by the age verification system 1102 is further described in in U.S. patent application Ser. No. 16/415,460, entitled "AUTHENTICATION AND AGE VERIFICATION FOR AN AEROSOL DELIVERY DEVICE,", which claims priority to U.S. Provisional App. No. 62/282,222 on Apr. 2, 2019, the entire disclosures of each of which are hereby incorporated by reference. The authentication described below may rely on age verification being performed first and then referenced for subsequent authentication using a control signal 1105 sent to the device 1106. However, there may be other verification mechanisms other than just for age. For example, in some embodiments, user identification may be performed in lieu of age verification. Cartridges or consumables may be registered as part of the age verification or authentication process as described in U.S. patent application Ser. No. 16/415,444, entitled "AGE VERIFICATION WITH REGISTERED CARTRIDGES FOR AN AEROSOL DELIVERY DEVICE," filed on May 17, 2019, the entire disclosure of which is herein incorporated by reference. U.S. Pat. No. 8,689,804 to Fernando et al. discloses identification systems for smoking devices, the disclosure of which is being incorporated herein by reference.

The age verification system 1102 may include a database that tracks users along with ages, as well as maintains a record of the devices and components (e.g. cartridges) along with approvals. It may be encrypted and/or use anonymous identifiers (e.g. numbers, letters, or any alphanumeric identifiers) for each user.

The initial age verification may occur and be stored in the database, such as may be maintained at the age verification system 1102 and/or otherwise accessible over the network 1103. In some embodiments, age verification records may be maintained using blockchain technology. Future age verification requests by that user may be confirmed by calling the database. Specifically, once a user is initially age verified as confirmed in the age verification system database, future verifications (i.e. "authentications") may be merely calls to this database for unlocking the device 1106. In other words, a user initially performs an age verification and then subsequent usage may require authentication without the complete initial age verification requirements. The frequency with which the device 1106 must be unlocked or authenticated can vary. Likewise, the timing for when a user needs to re-verify their age may vary. For example, each time the cartridge is replaced, the user may need to re-verify or re-authenticate. In some embodiments, the re-authentication may be required after a certain number of puffs from the device 1106 or may be based on the passage of time (e.g. once per hour, day, week, month, etc.). The online database may track the requests for authentication and set limits per user. This can prevent the potential fraud of a single user unlocking other under-age user's devices. This also would prevent the re-distribution of unlocked (i.e. verified and authenticated) devices and/or accessories. Reasonable limits for the number of devices, chargers, consumables, and/or authentications can prevent this potential fraud.

A user profile may be stored (e.g. on the device 1106 or from an application or app on a host device 1104) that includes an age verification as described with respect to FIG. 20. An app on the host device 1104 may access the user profile over a network, such as the network 1103. Once a user is initially age verified as confirmed in the age verification system database, the user profile for that user may be generated and saved so that future verifications (i.e. "authentications") may be merely calls to this database. In one embodiment, the age verification may be a prerequisite for the host device 1104 to be able to generate and submit the control signal 1105 to the device 1106.

The host device 1104 may be any computing device, such as a smartphone, tablet, or computer. The host device 1104 may communicate with or provide the control signal 1105 to the device 1106 for authentication. As discussed with respect to FIGS. 13-15, the control signal 1105 from the host device 1104 to the device 1106 may be an audio signal or a light/optical signal. In some embodiments, the host device 1104 may couple directly with the device 1106, such as to provide power or to communicate. The host device 1104 may be already configured to communicate over a network, such as the network 1103, so the device 1106 may not need the same level of communication functionality, since the host device 1104 provides for that capability. In one embodiment, the host device 1104, upon communication with the age verification system 1102, may provide the control signal 1105 to authenticate and unlock the device 1106.

The authentication may be a process for verifying a user's identity after that user has already verified their age. If the user does not verify their age, then the authentication process will fail. As described, the authentication process may include the device 1106 receiving and authenticating a control signal 1105 in order to unlock the device 1106. The age verification process may occur less frequently (e.g. at device purchase) than the authentication process, which may occur based on usage, such as based on puff frequency, puff length, time used, and/or each time the cartridge is replaced. In alternative examples, there may be a more frequent authentication process that is required. Failure of the authentication process may result in the device 1106 not operating. For example, if the control signal 1105 is not approved for use with the device 1106, then the device 1106 may be prevented from receiving electricity needed for heat.

The age verification system 1102 provides an indication as to whether a user is of an appropriate age for usage of a particular product, such as an aerosol delivery device or an electronic nicotine delivery systems ("ENDS") device including an aerosol delivery device, both of which are examples of the device 1106. At least some components or features of the age verification system 1102 may be part of the device 1106 or the host device 1104. For example, the processing and determinations from the age verification system 1102 may be performed locally after accessing a remote database. In an alternative embodiment, the age verification system 1102 may be located remotely and accessible over a network, such as the network 1103.

The present disclosure contemplates a computer-readable medium that includes instructions or receives and executes instructions responsive to a propagated signal, so that a device connected to a network can communicate voice, video, audio, images or any other data over a network. The device 1106, host device 1104 or the age verification system 1102 may provide the instructions over the network via one or more communication ports. The communication port may be created in software or may be a physical connection in hardware. The connection with the network may be a physical connection, such as a wired Ethernet connection or may be established wirelessly as discussed below. Likewise, the connections with other components may be physical connections or may be established wirelessly. The device 1106 or the host device 1104 may communicate through a network, including but not limited to the network 1103. For example, the signal detector circuitry 1202 (discussed with respect to FIG. 12) may include network functionality in order to be coupled with the host device 1104 or the age verification system 1102. These components may include communication ports configured to connect with a network, such as the network 1103.

The network (e.g. the network 1103) may couple devices so that communications may be exchanged, such as between the device 1106, the host device 1104, and/or the age verification system 1102, including between other wireless devices coupled via a wireless network, for example. As described a cluster of machines storing data to be analyzed may be connected over one or more networks, such as the network 1103. A network may also include mass storage, such as network attached storage (NAS), a storage area network (SAN), or other forms of computer or machine readable media, for example. A network may include the Internet, one or more local area networks (LANs), one or more wide area networks (WANs), wire-line type connections, wireless type connections, or any combination thereof. Likewise, sub-networks, such as may employ differing architectures or may be compliant or compatible with differing protocols, may interoperate within a larger network. Various types of devices may, for example, be made available to provide an interoperable capability for differing architectures or protocols. As one illustrative example, a router may provide a link between otherwise separate and independent LANs. A communication link or channel may include, for example, analog telephone lines, such as a twisted wire pair, a coaxial cable, full or fractional digital lines including T1, T2, T3, or T4 type lines, Integrated Services Digital Networks (ISDNs), Digital Subscriber Lines (DSLs), wireless links including satellite links, or other communication links or channels, such as may be known to those skilled in the art. Furthermore, a computing device or other related electronic devices may be remotely coupled to a network, such as via a telephone line or link, for example.

A wireless network may couple devices, such as the device 1106, the host device 1104 and the age verification system 1102. The network 1103 may include a wireless network and may employ stand-alone ad-hoc networks, mesh networks, Wireless LAN (WLAN) networks, wireless wide area network (WWAN), wireless metropolitan area network (WMAN), cellular networks, or the like. A wireless network may further include a system of terminals, gateways, routers, or the like coupled by wireless radio links, or the like, which may move freely, randomly or organize themselves arbitrarily, such that network topology may change, at times even rapidly. A wireless network may further employ a plurality of network access technologies, including Long Term Evolution (LTE), WLAN, Wireless Router (WR) mesh, or 2nd, 3rd, or 4th generation (2G, 3G, 4G, 5G, or future iterations) cellular technology, or the like. A network may enable RF or wireless type communication via one or more network access technologies, such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, 802.11b/g/n, Zigbee, Z Wave, IEEE 802.16 (e.g., WiMax) and/or other WWAN/WMAN technology, or the like, including future iterations of any of the aforementioned technologies. A wireless network may include virtually any type of wireless communication mechanism by which signals may be communicated between devices. In some embodiments, the communication protocols listed above may be used for communication between the device 1106 and the host device 1104, and the host device 1104 then communicates with the age verification system 1102 through the same or different communication protocols.

Signal packets communicated via a network, such as the network 1103 or a network of participating digital communication networks, may be compatible with or compliant with one or more protocols. Signaling formats or protocols employed may include, for example, TCP/IP, UDP, DECnet, NetBEUI, IPX, Appletalk, or the like. Versions of the Internet Protocol (IP) may include IPv4 or IPv6. The Internet refers to a decentralized global network of networks. The Internet includes local area networks (LANs), wide area networks (WANs), wireless networks, or long haul public networks that, for example, allow signal packets to be communicated between LANs. Signal packets may be communicated between nodes of a network, such as, for example, to one or more sites employing a local network address. A signal packet may, for example, be communicated over the Internet from a user site via an access node coupled to the Internet. Likewise, a signal packet may be forwarded via network nodes to a target site coupled to the network via a network access node, for example. A signal packet communicated via the Internet may, for example, be routed via a path of gateways, servers, etc. that may route the signal packet in accordance with a target address and availability of a network path to the target address. This signal packet communication may be applicable to the data communication between the as the device 1106, the host device 1104 and/or the age verification system 1102.

The device 1106 includes a signal detector 1107 that detects a signal. As shown, the control signal 1105 is communicated from the host device 1104 to the signal detector 1107, but the control signal 1105 could come from a source other than the host device 1104, including being transmitted directly over the network 1103 to the device 1106. The signal detector 1107 may be one example of the sensor 908 shown in FIG. 9. Example signal detectors 1107 are described with respect to FIGS. 14-15.

FIG. 12 illustrates an embodiment of signal detector circuitry 1202 that may be located on or coupled with the signal detector 1107. The signal detector circuitry 1202 can be used by the device 1106 for confirming that any received control signal 1105 is correct for authentication. The signal detector circuitry 1202, in addition to receiving and analyzing the control signal 1105, may also operate to perform the authentication or may also be used for the initial age verification. The signal detector circuitry 1202 may also be referred to as authentication circuitry and may include a processor 1204, a memory 1206, a translator 1207, and a switch 1208.

The processor 1204 in the signal detector circuitry 1202 may be on one or more chips and may include a central processing unit (CPU), a graphics processing unit (GPU), a digital signal processor (DSP) or other type of processing device. The processor 1204 may be one or more general processors, digital signal processors, application specific integrated circuits, field programmable gate arrays, servers, networks, digital circuits, analog circuits, combinations thereof, or other now known or later developed devices for analyzing and processing data. The processor 1204 may operate in conjunction with a software program, such as code generated manually (i.e., programmed).

The processor 1204 may be coupled with a memory 1206, or the memory 1206 may be a separate component. The memory 1206 may include, but is not limited to, computer readable storage media such as various types of volatile and non-volatile storage media, including random access memory, read-only memory, programmable read-only memory, electrically programmable read-only memory, electrically erasable read-only memory, flash memory, magnetic tape or disk, optical media and the like. The memory 1206 may include a random access memory for the processor 1204. Alternatively, the memory 1206 may be separate from the processor 1204, such as a cache memory of a processor, the system memory, or other memory. The memory 1206 may be an external storage device or database for storing recorded ad or user data. Examples include a hard drive, compact disc ("CD"), digital video disc ("DVD"), memory card, memory stick, floppy disc, universal serial bus ("USB") memory device, or any other device operative to store data, including authentication or signal detection data. The memory 1206 is operable to store instructions executable by the processor 1204.

The functions, acts or tasks illustrated in the figures or described herein may be performed by the programmed processor executing the instructions stored in the memory 1206. Specifically, the operation detecting the control signal 1105 and determining whether control signal 1105 can authenticate the device 1106 may be performed by the processor 1204 based on instructions from the memory 1206. In other embodiments, the authentication and/or age verification, such as from system 1102, may be performed by the processor 1204 based on instructions from the memory 1206. The functions, acts or tasks are independent of the particular type of instruction set, storage media, processor or processing strategy and may be performed by software, hardware, integrated circuits, firm-ware, microcode and the like, operating alone or in combination. Likewise, processing strategies may include multiprocessing, multitasking, parallel processing and the like.

The processor 1204 may be configured to execute software including instructions for receiving/analyzing the control signal 1105, authenticating the device 1106, and/or verifying a user's age or for subsequent authentication operations for the age verification system 1102. Specifically, if the processor 1204 cannot authenticate the control signal 1105, then the switch 1208 can be activated to prevent power from being provided which stops or prevents operation of the device 1106. Specifically, the device 1106 may include a battery for powering the device, which is only activated when the device 1106 receives the authenticated control signal 1105. In other words, the flow of electricity is allowed if authentication from age verification passes. Alternatively, the flow of electricity may be stopped if the authentication or age verification fails. Specifically, electricity is not provided to the device 1106 when the switch 1208 is turned off. The switch 1208 may be the switch 910 described with respect to FIG. 9. Although the switch 1208 is illustrated as part of the signal detector circuitry 1202, it could be a separate component on the device 1106 in alternative embodiments.

The signal detector circuitry 1202 may include a translator 1207 for translating the control signal 1105. The translation of the control signal 1105 may be part of the authentication process by which the control signal 1105 is authenticated. The translator 1207 may be different depending on the type of control signal 1105 as further described below with respect to FIGS. 13-15.

FIG. 13 illustrates embodiments of a control signal 1105. The control signal 1105 is provided for authentication of the device 1106. The control signal 1105 may correspond with a serial number of the device 1106 or a component (e.g. a cartridge) of the device. In order to be authenticated, the control signal 1105 must match the serial number. In alternative embodiments, rather than serial numbers, there may be another identification or authentication code for the device 1106. The code may be unique for each device 1106, for each user, or for each type of device, in alternative embodiments. The age verification system 1102 may include a database for storing the codes or control signals 1105 to be provided for authentication. The database may associate a user, a profile, and/or a device with a particular code that can unlock the device 1106. In one embodiment, the database may be a decentralized network storage using Blockchain technology as described in U.S. patent application Ser. No. 16/415,477, entitled "DECENTRALIZED IDENTITY STORAGE FOR TOBACCO PRODUCTS," filed on May 17, 2019, which claims priority to U.S. Provisional patent application Ser. No. 62/838,272, filed on Apr. 24, 2019, entitled "DECENTRALIZED IDENTITY STORAGE FOR TOBACCO PRODUCTS," the entire disclosures of each of which are incorporated by reference.

The control signal 1105 may be encrypted to decrease the likelihood of hacking by a non-verified user. In one embodiment, the serial number of the device 1106 or another identifier can be randomly assigned a hashed code during manufacturing which is stored in the device 1106 memory chip (e.g. memory 1206). The values may be stored in a database that is updated and accessed for authentication. In the embodiment of FIG. 19, the help desk operator can access this database. In that embodiment, when the operator receives a call from the device 1106 purchaser to unlock their device, the operator looks up the serial number and transmits the assigned hashed code. In an alternative embodiment, the host device 1104 can access the database for a particular entry once the user has been identified and/or age verified. In another encryption example, the serial numbers or identifiers may utilize a certain code operator that translates all the numbers the same way. For example, a set amount may be added to or subtracted from all serial integers and serial alphabetical characters. In that example where the set amount is +5, the identifier of S189A4R encrypted becomes X634F9W. For added security and complexity, the code may change based on the manufacturing date/time of the device 1106.

The device 1106 could be sold in the locked position which does not allow the device to be used until authentication, which may also include a registration with age verification. In one embodiment, kiosks which are positioned at the point of sale for retail could make it easier for consumers to register and age verify their device at the time of purchase. Once the consumer is age-verified, periodic authentication of the device is used to confirm the consumer. In other embodiments, retail clerks may also be utilized in the registration and age verification process, such as by scanning an identification documentation and prompting the device purchaser to give a visual or audible input that is used for authentication.

The device 1106 may incorporate a pseudorandom number generator that is synchronized with a network version, such as from the age verification system 1102 or associated with a help desk operator. This number generator may be rolling and changes after a predetermined amount of time. The control signal 1105 would not need to be linked to the device serial number. Other example forms of encryption may include the Advanced Encryption Standard (AES), Triple Data Encryption Standard (3DES), Twofish, or RSA techniques that can be used for encrypting the control signal 1105 to prevent unverified users from unlocking a device. These techniques can encrypt the control signal 1105 prior to sending it to the device 1106. The device 1106 could then decrypt the signal using an assigned key that is stored in the device 1106 memory 1206.

The control signal 1105 could be the same for every manufactured device or may be unique to a user, profile, or specific device. During the device manufacturing process, the device software may be encoded with a specific unlock sequence (i.e. the control signal 1105, including the audio signal 1302 and/or the optical signal 1304) that corresponds to its serial number or another identifier. In one example, the control signal 1105 may be an unlock tone sequence that is the device's serial number transcribed in accordance with a character encoding scheme, such as Morse code or Tap code.

The control signal 1105 from the host device 1104 to the device 1106 may be an audio signal 1302. The audio signal 1302 may include a tone sequence. The audio signal 1302 or tone sequence could be a series of pulses, such as long and short that are similar to Morse code. In alternative embodiments, different types of sequences may be used that have increases and/or decreases in amplitude and/or frequency. The serial number or identifier may be converted to authentication tone at the age verification system 1102 or through software used by an operator (e.g. help desk operator). This conversion may be through software. One example of such software may include a conversion into Morse code, such as the free online software at heaps://morsecode.scphillips-.com/translator.html. The translation of the serial number or identifier is a conversion into a series of dots and dashes for the Morse code example. Accordingly, the identifier S189A4R becomes . . . . . . . . . . . . .- . . . .- .-. This Morse code signal can be audibly played to the device 1106, which detects the code with the signal detector 1107 and translates the code with the translator 1207. The control signal 1105 may refer to the converted signal that is then translated back to the identifier by the device 1106.

The control signal 1105 from the host device 1104 to the device 1106 may be a light/optical/scanned signal 1304, which may be referred to as an optical signal. The optical signal 1304 may be a series of light pulses or a light sequence. Communication with an optical signal or light source is further described in the United Kingdom Application No. 1906243.9 entitled "ELECTRONIC VAPOUR PROVISION SYSTEM WITH OPTICAL WIRELESS COMMUNICATIONS," filed on Mar. 5, 2019 in the United Kingdom, which is hereby incorporated by reference.

FIG. 14 illustrates embodiments of the audio detector 1402. The audio detector 1402 is one embodiment of the signal detector 1107. The audio detector 1402 may include a pressure sensor 1407 and/or a microphone 1408. In some embodiments in which the device is a puff activated aerosol delivery device, the pressure sensor 1407 may include the existing pressure sensor in the device 1107 (e.g. sensor 908) that may be used to measure changes in pressure, such as when a user puffs or inhales on the device 1107 that activates the device 1107 (e.g. turns on the heater). There may be a separate pressure sensor that measures inhalation for activating the device, or there may just be one pressure sensor that activates the device on inhalation and is used for detecting the audio signal 1302. In other words, the pressure sensor 1407 could be the same one that is used to sense puffs and activate the heater, or a secondary pressure sensor could be used for authentication only.

The pressure sensor 1407 may be exposed to an external surface of the device 1107, such as by an orifice, port, or canal for improving detection of the audio signal 1302. In an embodiment where the audio signal 1302 is provided by a help desk employee (e.g. FIG. 19), the help desk employee may instruct the device purchaser to hold the phone speaker to the correct location, such as at the orifice, port, or canal, on the external surface of the device 1107 so that the pressure sensor 1407 is in the optimal location to sense the audio signal 1302 (i.e. authentication tone). In other embodiments where the audio signal 1302 is provided by an app or software on the host 1104 (e.g. computing device, mobile phone, tablet, etc.), the app can instruct the user how to hold the smartphone speaker in the optimal location relative the device 1107. This ensures that the pressure sensor 1407 can detect the audio signal 1302.

The audio signal 1302 may be referred to as an authentication tone and may be a low frequency pressure wave. In one embodiment, the wave may be on the lower end of functionality for a basic phone speaker that is used in most smartphones or cell phones. In one example, the frequency could be around 10 Hz-20 Hz in order for the pressure sensor 1407 to detect the tone with a reduced signal-to-noise ratio.

There may be many different embodiments of the pressure sensor 1407 that could detect the audio signal 1302. One example is a sealed differential pressure sensor that allows changes in the ambient pressure (due to pressure or sound waves) to be compared with a standard reference pressure. A sealed differential pressure sensor could detect sound waves emitted from a speaker. Alternatively, the pressure sensor 1407 may be an unsealed differential pressure sensor which includes a flow sensor that compares the pressure produced from a fluid stream passing by two apertures of different diameters. An unsealed differential pressure sensor may need to be arranged to better detect sound waves.

In another embodiment, the device 1107 might contain a microphone 1408. A microphone 1408 may be able to sense a wider range of tones (e.g. non-audible in addition to audible) tones that could be emitted by the cell phone speaker, but it would be an additional component. Specifically, audible tones may be the frequency range that is audible to humans, while the tones could further include a wider range, including non-audible tones. The microphone 1408 could be used to sense puffs and activate the heater, or there may be a secondary microphone for detecting the audio signal 1302 or authentication tone only. In this embodiment, the frequency may be on the upper end of the functionality of a smartphone, cell phone, tablet, or other common speakers, such as in the 20 kHz to 25 kHz range. Such a frequency would be inaudible to the user or device purchaser while still being sensed by the microphone 1408. The microphone 1408 could sense tones based on the limit of its functionality, including any audible frequencies in a range between approximately 20 Hz to 20 kHz.

There may be many different embodiments of the microphone 1408 that could detect the audio signal 1302. One example is a MEMS electret microphone which uses a PTFE-based film diaphragm. This example may be an appropriate size with longevity. In other examples, other electret microphones could be used. In addition, there are other microphones in the condenser microphone family. Other examples include a crystal or piezo microphone. These examples may sense noise or vibrations through solid objects and could be placed internally against the outer shell of the device, which may eliminate the need for an orifice, canal, or port to allow sound waves to travel into the device 1107.

FIG. 15 illustrates embodiments of an optical detector 1502. The optical detector 1502 is one embodiment of the signal detector 1107. The optical detector 1502 may also be referred to as a visual detector or a light detector. The optical detector 1502 may include a light sensor 1507, a photodiode 1508, a reader 1509, and/or an infrared detector 1510. The light sensor 1507 may include any light dependent resistive elements. These sensors may change in resistance due to the presence or absence of light. This may require current to flow through the resistive element when the optical signal 1304 (i.e. authentication light sequence) is being transmitted. The photodiode 1508 may include sensors that generate a small current when exposed to a light source. It may act as a switch and may have a quick response time.

The optical detector 1502 may include a reader 1509, such as a camera, barcode reader, or other detector. In one example, the user may capture a picture (e.g., with a host 1104, including a mobile device or smartphone) of a unique code (e.g. bar code) associated with the particular device. In alternative examples, the reader 1509 may read a bar code, a radio frequency (RF) identification, near-field communication (NFC) communication, a magnetic strip reader, a chip reader (e.g. similar to a credit card reader), wired communication, or wireless communication. Exemplary bar codes may include any type of scannable identifier, such as a universal product code (UPC), data matrix code, and/or a quick response (QR) code. The code may include any one-dimensional (1D) codes, two-dimensional (2D) codes, three-dimensional (3D) codes, or other types of codes. Exemplary communications and authentication with RFID are described in U.S. Pat. No. 10,015,987 to Henry et al., and U.S. Pat. Pub. No. 2017/0020191 to Lamb et al., each of which is hereby incorporated by reference. Exemplary communications and authentication with NFC is described in U.S. Pat. No. 9,864,947 to Sur et al., which is hereby incorporated by reference. The code, such as a barcode, can be printed on product packaging, on a label, on the product itself, or on an insert in the product packaging. In one embodiment, there may be a unique barcode for each particular device. The application or website linked from the barcode may use software to convert identification information extracted from the unique barcode to the corresponding authentication light sequence. In other words, the scanning of the barcode can trigger the emission of the optical signal 1304 by the host 1104. Alternatively, the application or website may look up identification information extracted from the unique barcode in a database to determine the appropriate optical signal 1304 for that particular device 1106. In another embodiment, the device 1106 (or packaging/inserts of the device 1106) may carry an RFID tag that can be read by the host 1104 (e.g. mobile device or smartphone) executing an application or capable of accessing the website. The RFID tag may carry a unique identifier for the device 1106 that can result in generation of the optical signal 1304 that can authenticate or unlock that particular device 1106.

For the optical detector 1502 sensor examples, the light wavelength range may be approximately 400 nm to 700 nm. The optical detector 1502 may be tuned to receive a smaller range or wavelengths or any/all (i.e. white light). As opposed to a series of pulses, the optical signal 1304 may include a pattern of wavelengths. In one example, the optical signal 1304 may climb from 400 nm to 500 nm in 3 seconds, remain black for 5 seconds, then climb from 400 nm to 700 nm in 1 second. This variation of wavelength and time can be used to generate unique optical signals 1304. Other patterns and wavelength variations may be used.

When the host 1104 is a mobile device or smartphone, the optical signal 1304 may be generated by the display (e.g. light/color arrangement on the screen or pulses from the display) or by a flashlight (e.g. a rear facing flashlight on a mobile device or other computing device). The display example may include the display being mostly black but including a portion that is put near the optical detector 1502 of the device 1106 for detecting any colors/pulses/patterns that are shown in the display screen. In the example of the host 1104 including a flashlight application, an app could be programmed to cause the flashlight to transmit light according to a specific pattern or sequence that provides the optical signal 1304. The intensity of light may be greater for a flashlight which may lower the chance of signal loss during transmission. Prior to the optical signal 1304 transmission, the app may prompt the user to position their device in the correct location such that the optical detector 1502 is aligned with the flashlight on the host 1104 or mobile device. The optical detector 1502 may include a reader 1510 for scanning a QR or other bar code that is displayed on the app or webpage which corresponds to age verification with the age verification system 1102. The reader 1510 of such embodiments scans this QR code which enables the device to be unlocked.

The light sensor on the device could be an infrared (IR) sensor 1510 in one embodiment. The host 1104 may be a mobile phone or other IR enabled device that communicates the optical signal 1304 via IR. In some embodiments, there may be a combination of the visible light spectrum and IR, which may rely on different optical detectors 1502 (e.g. light sensor 1507 and IR 1510) or a single sensor may measure both. Having a combination of optical types may provide for a larger set of code combinations for the optical signal 1304. The user may be able to see the visible light spectrum, while the IR may not be detectable which could also improve security by preventing recreation of the optical signal. For an IR or non-visible signal, the user may be provided with an indication (e.g. a visual spectrum pulse) or confirmation that the optical signal 1304 is being communicated for controlling/unlocking the device.

FIG. 16 illustrates an example system diagram for functional control of a device with an audio signal. Similar to FIG. 11, FIG. 16 illustrates the system for audio detection. The host 1104 can access the age verification system 1102 over the network 1103. Upon verification, the host 1104 can be used for authentication of the device 1106. Specifically, the host 1104 can provide an audio signal 1302 to the device 1106 for detection by an audio detector, such as pressure sensor 1407 and/or a microphone 1408. The audio signal 1302 is a control signal or authentication signal for unlocking the device 1106. In other embodiments, the audio signal 1302 may be provided by a help desk call, rather than a user's smartphone or mobile device. In such an embodiment, the host 1104 may be considered to be a help desk that is accessed through audio communication (e.g. VoIP or telephone call).

FIG. 17 illustrates an example system diagram for functional control of a device with an optical signal. Similar to FIG. 11, FIG. 17 illustrates the system for optical/visual detection. The host 1104 can access the age verification system 1102 over the network 1103. Upon verification, the host 1104 can be used for authentication of the device 1106. Specifically, the host 1104 can provide an optical signal 1304 to the device 1106 for detection by the optical detector 1502. The optical signal 1304 is a control signal or authentication signal for unlocking the device 1106. Examples of the optical detector 1502 are illustrated in and described with respect to FIG. 15.

FIG. 18 is a flow chart illustrating one example of the control signal process. In block 1802, a user/consumer purchases a device, such as device 1106. The purchase may be made online or in-person at a retailer or kiosk. The device can operate until authentication is required in block 1804. In one embodiment, the device may be in a locked or non-operational state until authentication is completed. In another embodiment, the device 1106 may be sold unlocked for a limited use (limited time, or limited puffs) after which time authentication will be required. Authentication may first require an age verification as in block 1806, which may be performed by the age verification system 1102. Age verification may only occur once or may need to be updated periodically, whereas authentication may be required more frequently (e.g. each time the cartridge or other aerosol source member is replaced). The age verification system 1102 provides functionality for verifying the age of a user. The age verification may be for a particular user such that the verification applies for multiple devices used by that user, but may still require authentication for each individual device. In some embodiments, each device may require the age verification process in addition to subsequent authentications.

As an initial age verification, the age verification system 1102 may require some identification documentation to establish the age of a user. For example, a driver's license or passport may be uploaded to establish a user's age. The image from that documentation may be used for future age verification by performing facial recognition using that image. Facial recognition technology can analyze the two images to either confirm identity match, reject identity verification, or flag the verification to request additional identification information. This age verification may include comparing that image to a live self-image ("selfie") or video that the user takes with their mobile device or webcam. This may prevent fraud of merely showing a picture of someone. Specifically, this reduces the potential for using a hard-copy photo to trick the facial recognition software (e.g., holding up the driver's license close to the webcam). The selfie image that the user uploads can also be checked for liveliness by recording a short video to ensure that the frames change. In alternative embodiments, the verification step may include an audible input from the user, such as recitation of a number, sequence, or code to verify liveliness. Other age verification examples may include some form of a fingerprint reader for verifying the user after that user has been age verified. In one embodiment, the host 1104 may receive the fingerprint as part of the verification process. There may be other biometrics that are used for verifying a user, such as DNA, blood, or other biological indicators.

The device 1106 may require more frequent authentications to ensure that a device is not age verified and then distributed to other users. The authentication may include providing a control signal to the device 1106 as in block 1808. As described, the control signal may be either an audio signal 1302 or an optical signal 1304. That signal may originate from a host device 1104 or from another source (e.g. help desk call). The control signal is received at the device 1106 in block 1810 and if the control signal is correct, then the device is authenticated and the device can continue to be used until authentication is required again in block 1812. If the control signal received at the device 1106 is not correct in block 1810, then the device 1106 is not authenticated and will remain locked until a correct authentication control signal is sent in block 1808.

In some embodiments, the authentication of the device through the control signal unlocks the device for the particular user and the future authentications that may be required again may be performed on the device 1106 itself. For example, the biometric, fingerprint reader, or other biological indicators described above may be used on the device for authenticating. In this regard, in some embodiments, the device 1106 may be tied (e.g., upon the initial authentication) to a particular user biometric(s) used for the initial authentication to prevent a second user from using the device 1106. When re-authentication is required in the future, the user may unlock and/or continue use of the device 1106 by providing the user biometric(s) to re-authenticate. As a further example, the user may set a code, such as a pin code that may be entered via a user interface of the device 1106 (e.g., through a touchscreen, input button, a particular pattern of puffs that may be provided by the user puffing on the device, etc.) and/or via a computing device that may be communicatively coupled to the device 1106 when the device 1106 is initially authenticated and may later enter the pin code to re-authenticate the user to unlock and/or continue use of the device 1106.

FIG. 19 is a flow chart illustrating one example of the audio signal process. The example shown in FIG. 19 is use of a help desk for verification and authentication of the device 1106. Specifically, a user can call a help desk line for the verification and/or authentication. In block 1902, the user calls the help desk for age verification. The help desk phone call can be used to confirm identity by providing or confirming user information. The help desk employee takes the device purchaser's information, which could include device serial number, date of purchase, driver's license number, last four digits of social security number, or other personal information that could be used to verify the identity of the purchaser. In one embodiment, the help desk can be used to confirm information provided in an identification document to verify a user's age in block 1904. The help desk operator can then transmit an audio signal 1302 for the user to provide to the device 1106. Specifically, the user's phone receiver, which may be the host device 1104, has a speaker through which the audio signal 1302 or authentication tone is transmitted in block 1906.

In some embodiments, the help desk phone call in block 1902, the help desk verification in block 1904, and the authentication tone in block 1906 could all be from different devices or from the same device. For example, the verification phone call in blocks 1902-1904 may be made from a different phone than the source of the authentication tone. Specifically, the help desk could send or provide authorization for the authentication tone being transmitted from a different device or from a different source than the phone call with the help desk. In one example, the authorization tone may be played through an app on the phone (rather than playing it through the speaker during the phone call) based on the help desk verifying/authenticating the user. In another example, the help desk could send a one-time usable link to an audio file with the authentication tone, such as through an email, text message, or notification. The link may only be valid for a limited amount of time to prevent fraud.

The tone generation may be from software that could be incorporated into a mobile app or web app that the device purchaser uses themselves (e.g. through an app with a profile on a mobile device as in FIG. 20). The authentication tone would be generated and emitted though the user's computer, telephone, or mobile phone speakers, and detected by the audio detector 1402 of the device 1106 as in block 1908. If the authentication tone is not correct in block 1908, the device will remain locked or unauthenticated and wait for a correct authentication tone from block 1906. If the authentication tone is correct, then the device 1106 can be used until authentication is required again as in block 1910. In addition to the re-authentication process, there could be a requirement that the device purchaser re-verifies before every use, every charge, after a predetermined length of time, after a predetermined amount of puff-second or puffs, prior to a predetermined number of cartridge insertions, or just a single verification after device purchase. In such examples, when the authentication is required again in block 1910, the user's age may need to be re-verified in block 1904 in addition to the authentication in block 1906.

FIG. 20 is a flow chart illustrating one example of authentication with a host device. The embodiment in FIG. 20 authenticates the device 1106 in part based on a profile of an age verified user than can be accessed for authentication. In block 2002, the device 1106 is purchased by a user. The user provides identification for the age verification system in block 2004. As discussed above, the identification may include information that is used to confirm a user's identity and age. That information may be showing an identification (e.g. driver's license) to a retailer or scanning the identification at a kiosk or on the user's personal device, such as a computer or mobile device. The user might also utilize an internet-connected age-verification system (computer, mobile phone, etc.) to upload their identification information themselves. Upon the identification and age verification, the user can create a user profile with the age verification system 1102 in block 2006. The age verification system 1102 may be connected over a network 1103, such as the Internet, may require the user to create a profile in an application, or with a web-based application. The user profile can be stored in a database for the age verification system 1102 for quick access during future authentication requests. Based on a request and conformation that the user (or user's profile) verifies the user's age, the host device 1104 can send a control signal 1105 to the device 1106 as in block 2008. The control signal 1105 may be stored and associated with the user profile stored in a database. Alternatively, there may be an application that generates the correct control signal based on the information stored in the user profile including information about the device 1106 (e.g. serial number). The control signal 1105 can be an audio signal 1302 or an optical signal 1304 that is transmitted by the host device 1104. If the control signal is not correct in block 2010, the device 1106 is not authenticated and must wait for the correct control signal. If the control signal is correct in block 2010, the device 1106 can be used until authentication is required again in block 2012. When authentication is again required, the host device can again send a control signal to the device in block 2008.

FIG. 21 illustrates an example authentication key 2102. The authentication key 2102 may be sold as a part of the packaging with the device. The authentication key 2102 may be used with the optical signal 1304 by easily aligning with the optical detector 1502 (e.g. the light sensor 1507) on the device 1106 and obstructs the amount of light or obstructs certain segments of light that are distinguishable by the detector or sensor. The authentication key 2102 may incorporate a rotating mechanism that changes the light intensity allowed to the detector/sensor or changes the segments of light that can pass to the detector/sensor. In one embodiment, a range of numbers (e.g. from 0-12) are listed on the circumference of the key. As the rotating mechanism is engaged, the numbers may also rotate compared to an arrow that helps the device user identify to which number the key is set. In this embodiment, a user can unlock the device 1106 without having access to a network or the Internet. As described above, the user can first perform an age verification (e.g. the user calls the help desk to age verify over the phone). After age verification, a number or sequence of numbers may be provided for use with the authentication key 2012. The numbers or sequence of numbers is for the rotation of the authentication key 2012. In one embodiment, the number or sequence of numbers may correspond to the serial number of the device 1106. The corresponding light sequence generated from the user rotating the key may be programmed into the memory of the device 1106 (e.g. in the memory 1206), such as during chip manufacturing. This may allow the processor (e.g. processor 1204) to compare the expected value saved in the memory with the received value from the single or multiple rotations of the authentication key 2102 and compare the two to determine authentication.

The foregoing description of use of the article(s) can be applied to the various example implementations described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article(s) illustrated in FIGS. 1-21 or as otherwise described above may be included in an aerosol delivery device according to the present disclosure.

Many modifications and other implementations of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific implementations disclosed, and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:
1. A system comprising:
a consumable comprising an aerosol source material, the consumable being associated with readable information corresponding to a serial number assigned to the consumable;

a host device comprising a communications interface, wherein the host device is configured to:
  transmit a request and receive an age verification confirmation for a user via the communications interface,
  read the readable information corresponding to the serial number of the consumable via the communications interface, and
  output a control signal comprising an indication of the age verification confirmation and information corresponding to the serial number of the consumable that is based on the readable information;
an aerosol delivery device comprising processing circuitry and signal detector operably coupled to the processing circuitry, the aerosol delivery device being configured to receive the consumable as a removably installed component;
wherein the processing circuitry is configured to:
  transition the aerosol delivery device into a locked state in response to detecting installation of the consumable to the aerosol delivery device;
  receive the control signal from the host device via the signal detector, the control signal comprising the indication of the age verification confirmation and the information corresponding to the serial number of the consumable; and
  transition, in response to receipt of the control signal from the host device, the aerosol delivery device out of the locked state to permit delivery of an aerosol, by the aerosol delivery device using the aerosol source material from the consumable.

2. The system of claim 1, wherein the readable information is a bar code or a magnetic strip.

3. The system of claim 1, wherein the readable information is readable from a wireless communication.

4. The system of claim 1, wherein the wireless communication is from a radio frequency identification (RFID) tag or a near-field communications (NFC) tag.

5. The system of claim 1, wherein the processing circuitry is configured to transition back into the locked state in response to one or both of: (a) reaching a time limit or (b) reaching a number of puffs.

6. The system of claim 1, wherein the host device outputs the control signal as an optical signal; and
  wherein the host device is further configured to display a prompt to the user indicating alignment positioning of a light source of the host device with the signal detector of the aerosol delivery device.

7. The system of claim 1, wherein the host device is configured to capture an image in association with the age verification confirmation.

8. The system of claim 7, wherein the age verification confirmation is based in part on facial recognition processing of the image.

9. The system of claim 1, further comprising an age verification system, the age verification system being configured to:
  receive the request for the age verification confirmation;
  access, based on the request, an existing user profile for the user, the existing user profile indicating that an age verification has previously been performed for the user;
  in response to determining that the existing user profile indicates that the age verification has been previously performed for the user, perform an identity verification based on information within the request; and
  transmit the age verification confirmation in response to successfully performing the identify verification.

10. The system of claim 1, wherein the host device is further configured to capture an image of identification documentation for the user and transmit the image of the identification documentation in the request.

11. A method for controlling operation of an aerosol delivery device, the method comprising:
  transmitting, by a host device via a communications interface, a request for an age verification confirmation of a user;
  receiving the age verification confirmation for the user at the host device in response to the request;
  reading, via the communications interface, readable information corresponding to a serial number assigned to the consumable, wherein the consumable comprises an aerosol source material for delivery in an aerosol by the aerosol delivery device; and
  outputting, by the host device for receipt by a signal detector of the aerosol delivery device, a control signal comprising an indication of the age verification confirmation and information corresponding to the serial number of the consumable based on the readable information, wherein, in response to receipt of the control signal, the aerosol delivery device transitions out of a locked state to permit aerosol delivery by the aerosol delivery device from the consumable, the aerosol delivery device having entered the locked state that prevents aerosol delivery in response to installation of the consumable to the aerosol delivery device.

12. The method of claim 11 further comprising transitioning back into the locked state in response to one or both of: (a) reaching a time limit or (b) reaching a number of puffs.

13. The method of claim 11, wherein the control signal is an optical signal; and
  wherein the method further comprises displaying a prompt to the user indicating alignment positioning of a light source of the host device with the signal detector of the aerosol delivery device.

14. The method of claim 11 further comprising capturing an image, by a camera of the host device, in association with the age verification confirmation.

15. The method of claim 14 wherein the age verification confirmation is based in part on facial recognition processing of the image.

16. The method of claim 14 further comprising including the image in the request for the age verification confirmation.

17. The method of claim 11 further comprising:
  capturing, by the host device, an image of identification documentation for the user; and
  transmitting the image of the identification documentation in the request.

18. A host device comprising:
communications circuitry; and
processing circuitry operably coupled to the communications circuitry;
wherein the processing circuitry is configured to:
  transmit, via the communications circuitry, a request for an age verification confirmation of a user;
  receive the age verification confirmation for the user in response to the request;
  read, via the communications circuitry, readable information corresponding to a serial number assigned to the consumable, wherein the consumable comprises an aerosol source material for delivery in an aerosol by an aerosol delivery device; and output, by the communications circuitry for receipt by a signal detector of the aerosol delivery device, a control signal comprising an indication of the age verification confirmation and information corresponding to the serial number of the consumable based on the readable information, wherein, in response to receipt of the control signal, the aerosol delivery device transitions out of a locked state to permit aerosol delivery by the aerosol delivery device from the consumable, the aerosol delivery device having entered the locked state that prevents aerosol delivery in response to installation of the consumable to the aerosol delivery device.

19. The host device of claim 18, wherein the processing circuitry is further configured to:

perform a facial recognition capture of a face of the user via a camera of the host device; and include information based on the facial recognition capture in the request.

20. The host device of claim 18, wherein the control signal is an optical signal.

21. The system of claim 1, wherein the control signal is provided via a link from the host device to the aerosol delivery device, and wherein the link is only valid for a limited amount of time.

22. The method of claim 11, wherein the control signal is provided via a link from the host device to the aerosol delivery device, and wherein the link is only valid for a limited amount of time.

\* \* \* \* \*